United States Patent
Kagechika

(10) Patent No.: US 7,259,187 B2
(45) Date of Patent: Aug. 21, 2007

(54) TROPOLONE DERIVATIVES

(75) Inventor: Hiroyuki Kagechika, Tokyo (JP)

(73) Assignee: Research Foundation Itsuu Laboratory, Tokyo (JP)

( * ) Notice: Subject to any disclaimer, the term of this patent is extended or adjusted under 35 U.S.C. 154(b) by 133 days.

(21) Appl. No.: 10/450,836

(22) PCT Filed: Dec. 18, 2001

(86) PCT No.: PCT/JP01/11083

§ 371 (c)(1),
(2), (4) Date: Dec. 16, 2003

(87) PCT Pub. No.: WO02/053523

PCT Pub. Date: Jul. 11, 2002

(65) Prior Publication Data

US 2004/0082550 A1 Apr. 29, 2004

(30) Foreign Application Priority Data

Dec. 26, 2000 (JP) ............................. 2000-394338

(51) Int. Cl.
*A61K 31/18* (2006.01)
*C07C 303/00* (2006.01)
(52) U.S. Cl. ........................ 514/601; 514/675; 564/80; 564/123; 564/161; 568/303
(58) Field of Classification Search .................. 564/80, 564/123, 161; 568/303; 514/601, 675
See application file for complete search history.

(56) References Cited

U.S. PATENT DOCUMENTS

| 3,391,133 A | 7/1968 | Donaruma |
| 3,424,841 A | 1/1969 | Donaruma |
| 5,235,076 A | 8/1993 | Asato et al. |
| 5,990,136 A | 11/1999 | Barbachyn et al. |
| 6,093,736 A | 7/2000 | Barbachyn et al. |

FOREIGN PATENT DOCUMENTS

| JP | 43-14705 | | 6/1943 |
| JP | 46-2574 | | 1/1971 |
| JP | 57-50934 | | 3/1982 |
| JP | 61-22047 | | 1/1986 |
| JP | 61-76440 | | 4/1986 |
| JP | 61215341 | * | 9/1986 |
| WO | 92/21643 | | 12/1992 |
| WO | 95/04036 | | 2/1995 |
| WO | 98/07708 | | 2/1998 |

OTHER PUBLICATIONS

Vieillescazes et al., 1985, CAS: 103:37118.*
Vieillescazes et al., Heterocycles, 1985, 23(4), 927-30.*
Ebisawa et al., Chemical & Pharmaceutical Bulletin, 2001, 49(4): 501-503.*
Yamato, 1987, CAS:106:66807.*
Bagli et al., J. of Medicinal Chemistry, 1979, 22(10): 1186-1193.*
Masayuki Ebisawa et al., "Novel Retinoidal Tropolone Derivatives. Bioisosteric Relationship of Tropone Ring with Benzoic Acid Moiety in Retinoid Structure", Chem. Pharm. Bull., vol. 49, No. 4, pp. 501-503 (2001).
English Language Abstract of JP 57-50934.
English Language Abstract of JP 61-22047.
English Language Abstract of JP 61-76440.
Yamazaki, M. et al., "Studies on Tropolone Derivatives Having Monoamine Oxidase Inhibitory Activity," *Yakugaku Zasshi*, vol. 108, No. 8, pp. 754-757, 1988.
Ang, K.H. et al., "A/C-Ring Colchicine Analogues: a Comparison of Molecular Conformations of the Minimized and Crystal Structures," *Aust. J. Chem.*, vol. 50, pp. 115-122, 1997.
Barnard, J.F. et al., "Small Molecule Probes of Glyoxalase I and Glyoxalase II," *Biochimica et 1994. Biophysica Acta*, vol. 1208, pp. 127-135.
Ferguson, L.R. et al., "Three Consistent Patterns of Response to Substituted Acridines in a Variety of Bacterial Tester Strains Used for Mutagenicity Testing," *Mutation Research*, vol. 157, pp. 29-37, 1985.
Takahashi K. et al., "Synthesis of 5-(1,3-Dithiol-2-Ylidene)-3, 6-Cycloheptadiene-1, 2-Dione ( or 7,10-Dithiasesquifulvalene-3,4-Quinone).Derivatives," *Chem. Lett.*, pp. 1505-1508, 1977.
Tsunetsugu J. et al., "The Synthesis of 4- and 5-(α- and β-Naphthyl) Tropolones," *Bull. Chem. Soc. Jap.*, vol. 49, No. 3, pp. 831-832, 1976.

(Continued)

*Primary Examiner*—Rebecca Anderson
*Assistant Examiner*—Rei-tsang Shiao
(74) *Attorney, Agent, or Firm*—Greenblum & Bernstein, P.L.C.

(57) ABSTRACT

Tropolone derivatives represented by the formula (I), which have retinoid actions and are useful as active ingredients of medicaments [$R^1$ to $R^4$ represent hydrogen atom, an alkyl group, or an alkoxyl group; the ring represented by Ar represents an aryl ring or a heteroaryl ring; X represents a single bond, —N=N—, —CON($R^5$)—, —(C=C)$_n$CON($R^6$)—, —N($R^7$)CON($R^8$)—, —SO$_2$N($R^9$)—, —N($R^{10}$)— ($R^5$ to $R^9$ represent hydrogen atom or an alkyl group, n represents 1 to 3, $R^{10}$ represents hydrogen atom, an alkyl group, or an acyl group), an alkylene group, an aryldiyl group, or a heterocyclic diyl group; Y represents hydrogen atom, —O$R^{11}$ ($R^{11}$ represents hydrogen atom, an alkyl group, or an acyl group), —NH$R^{12}$ ($R^{12}$ represents hydrogen atom, an alkyl group, an acyl group, or amino group), or a halogen atom

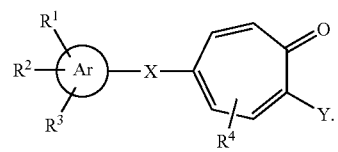

9 Claims, No Drawings

OTHER PUBLICATIONS

Kagechika, H. et al., "Retinobenzoic Acids. 1. Structure-Activity Relationships of Aromatic Amides with Retinoidal Activity," *J. Med. Chem.*, vol. 31, p. 2182, 1988.

Evans, R. M. et al., "The Steroid and Thyroid Hormone Receptor Superfamily," *Science*, vol. 240, p. 889, 1988.

Hashimoto, Y., "Retinobenzoic Acids and Nuclear Retinoic Acid Receptors," *Cell Structure and Function*, vol. 16, pp. 113-123, 1991.

Hashimoto, Y. et al., "Expression of Retinoic Acid Receptor Genes and the Ligand-Bind Selectivity of Retinoic Acid Receptors," *Biochemical and Biophysical Research Communications*, vol. 166, pp. 1300-1307, 1990.

* cited by examiner

TROPOLONE DERIVATIVES

TECHNICAL FIELD

The present invention relates to tropolone derivatives having retinoid actions and useful as active ingredients of medicaments.

BACKGROUND ART

Retinoic acid (vitamin A acid), an active metabolite of vitamin A, has extremely important physiological functions, e.g., inducing differentiation of immature cells under development processes toward mature cells having specific functions, enhancement of cell proliferation, and life support action. It has been revealed that various vitamin A derivatives synthesized so far also have similar physiological functions, for example, the benzoic acid derivatives disclosed in Japanese Patent Unexamined Publication (KOKAI) Nos. (Sho)61-22047/1986 and (Sho)61-76440/1986, and the compounds described in Journal of Medicinal Chemistry, 1988, Vol. 31, No. 11, p.2182. "Retinoids" is a general term for retinoic acid and the aforementioned compounds having retinoic acid-like biological activities.

For example, it was proved that all-trans retinoic acid binds as a ligand to the retinoic acid receptor (RAR) present in cellular nucleus, which belongs to the intranuclear receptor super family (Evans, R. M., Science, 240, p.889, 1988), and regulates proliferation and differentiation of animal cells or cellular mortalities (Petkovich, M., et al., Nature, 330, pp.444-450, 1987). It has also been suggested that the aforementioned compounds having the retinoic acid-like biological activities, e.g., 4-[(5,6,7,8-tetrahydro-5,5,8,8-tetramethyl-2-naphthalenyl)carbamoyl]benzoic acid: Am80, also bind to RAR in similar manners to retinoic acid to exhibit their physiological actions (see, Hashimoto, Y., Cell Struct. Funct., 16, pp.113-123, 1991; Hashimoto, Y., et al., Biochem. Biophys. Res. Commun., 166, pp.1300-1307, 1990).

Clinically, these compounds were found to be useful for therapeutic and preventive treatments of vitamin A deficiency disease, hyperkeratosis of epithelial tissue, rheumatism, delayed allergy, bone diseases, leukemia and certain types of cancer. However, because of variety of biological activities of these retinoids, they are not fully satisfactory medicaments from a viewpoint of side effect. Therefore, it has been desired to create retinoids having characteristic activities.

DISCLOSURE OF THE INVENTION

An object of the present invention is to provide novel compounds having retinoid actions and useful as active ingredients of medicaments. It has conventionally been considered that a partial structure of p-substituted benzoic acid (and carboxylic acid having an aromatic 6-membered ring of a structure similar thereto) is essential for activity expression of compounds having potent retinoid actions such as Am80. In order to achieve the foregoing object, the inventor of the present invention conducted various researches for novel compounds having no carboxyl group. As a result, the inventor found that the tropolone derivatives represented by the following general formula had desired retinoid actions. The present invention was achieved on the basis of the above finding.

The present invention thus provides compounds represented by the following general formula (I):

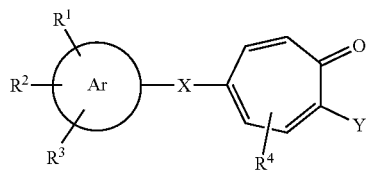

wherein, $R^1$, $R^2$, $R^3$ and $R^4$ independently represent hydrogen atom, a $C_{1-10}$ alkyl group (said alkyl group may be substituted), or a $C_{1-6}$ alkoxyl group, and when $R^2$ and $R^3$ are adjacent to each other, they may combine together with carbon atoms of the phenyl group to which $R^2$ and $R^3$ bind to form a 5- or 6-membered ring (said ring may have one or more $C_{1-4}$ alkyl groups or one condensed benzene ring which may have one or more substituents on the ring); the ring represented by Ar represents an aryl ring or a heteroaryl ring; X represents a single bond, —N=N—, —CON($R^5$)— (wherein $R^5$ represents hydrogen atom or a $C_{1-6}$ alkyl group), —(C=C)$_n$CON($R^6$)— (wherein n represents an integer of 1 to 3, and $R^6$ represents hydrogen atom or a $C_{1-6}$ alkyl group), —N($R^7$)CON($R^8$)— ($R^7$ and $R^8$ represent hydrogen atom or a $C_{1-6}$ alkyl group), —SO$_2$N($R^9$)— ($R^9$ represents hydrogen atom or a $C_{1-6}$ alkyl group), —N($R^{10}$)— ($R^{10}$ represents hydrogen atom, a $C_{1-6}$ alkyl group, or a $C_{1-6}$ acyl group), a $C_{1-6}$ alkylene group (said alkylene group may contain one or more unsaturated bonds or a cyclic structure), an aryldiyl group, or a heterocyclic diyl group; Y represents hydrogen atom, —OR$^{11}$ ($R^{11}$ represents hydrogen atom, a $C_{1-6}$ alkyl group, or a $C_{1-6}$ acyl group), —NHR$^{12}$ ($R^{12}$ represents hydrogen atom, a $C_{1-6}$ alkyl group, a $C_{1-6}$ acyl group, or amino group), or a halogen atom, or salts thereof. According to a preferred embodiment of the aforementioned invention, the compounds or the salts thereof, wherein $R^4$ is hydrogen atom or a $C_{1-6}$ alkyl group, Y is hydrogen atom, hydroxyl group, a $C_{1-6}$ alkoxyl group, hydrazino group, or a halogen atom are provided.

From another aspect, the present invention provides medicaments comprising the compounds represented by the aforementioned general formula (I) or physiologically acceptable salts thereof. These medicaments can be used as agents for suppressing action of a physiologically active substance which binds to an intranuclear receptor belonging to the intranuclear receptor super family to exhibit the physiological action.

The present invention further provides use of the compounds represented by the aforementioned general formula (I) or physiologically acceptable salts thereof for manufacture of the aforementioned medicaments, and methods for suppressing action of a physiologically active substance which binds to an intranuclear receptor belonging to the intranuclear receptor super family to exhibit the physiological action, which comprises the step of administering an effective amount of the compounds represented by the aforementioned general formula (I) or physiologically acceptable salts thereof to a mammal including human.

BEST MODE FOR CARRYING OUT THE INVENTION

In the present specification, the alkyl group may be a linear, branched or cyclic alkyl group, or an alkyl group consisting of a combination thereof. Alkyl moieties of the other substituents having the alkyl moiety (an alkoxyl group and the like) have the same meaning. The halogen atom referred to herein may be any of fluorine atom, chlorine atom, bromine atom, and iodine atom.

The groups represented by $R^1$, $R^2$, $R^3$ and $R^4$ may bind at an arbitrary position on the ring. As for the $C_{1-10}$ alkyl group represented by $R^1$, $R^2$, $R^3$ and $R^4$, examples of the alkyl group include, for example, methyl group, ethyl group, propyl group, isopropyl group, butyl group, isobutyl group, sec-butyl group, tert-butyl group, pentyl group, isopentyl group, neopentyl group, hexyl group, heptyl group, octyl group, nonyl group, decyl group and the like. When the alkyl group represented by $R^1$, $R^2$, $R^3$ and $R^4$ has a substituent, the type of the substituent is not particularly limited. However, a halogen atom, more preferably fluorine atom and the like can be used as the substituent. When $R^2$ and $R^3$ combine together with carbon atoms of the phenyl group to which $R^2$ and $R^3$ bind to form a 5- or 6-membered ring, the formed ring is preferably a 6-membered ring. When the ring has a $C_{1-4}$ alkyl group on the ring, methyl group is preferred as the alkyl group. Two to four methyl groups, for example, may exist on the ring.

The aryl group represented by Ar may be a monocyclic aryl group or a condensed aryl group, and a 6- to 14-membered aryl group can be used. More specifically, examples include, for example, phenyl group, naphthyl group, anthryl group, pyrenyl group and the like. Aryl moieties of other substituents having the aryl moieties have the same meaning. The aryl group represented by Ar is preferably a monocyclic aryl group, and most preferably phenyl group.

Type and number of heteroatoms contained in the heteroaryl group represented by Ar are not particularly limited. A heteroaryl group containing one or more heteroatoms selected from the group consisting of nitrogen atom, oxygen atom and sulfur atom as ring-constituting atoms is preferred. When two or more heteroatoms are contained, they may be the same or different. The heteroaryl group may be a monocyclic heteroaryl group or a condensed heteroaryl group. More specifically, examples include, for example, pyridyl group, pyrimidinyl group, pyrazinyl group, pyridazinyl group, triazinyl group, quinolyl group, isoquinolyl group, quinazolinyl group, phthalazinyl group, quinoxalinyl group, naphthylidinyl group, cinnolinyl group, thienyl group, furyl group, pyrrolyl group, imidazolyl group, pyrazolyl group, triazolyl group, tetrazolyl group, oxazolyl group, thiazolyl group, thiadiazolyl group, benzothienyl group, benzofuryl group, indolyl group, indazolyl group, benzimidazolyl group, benzotriazolyl group, benzoxazolyl group, benzothiazolyl group, purinyl group and the like. Among them, benzothienyl group is preferred.

When X represents a single bond, the tropolone ring and the aryl ring or heteroaryl ring represented by Ar are directly bound to each other without atom or group. When X represents —CON($R^5$)—, $R^5$ is preferably hydrogen atom. When X represents —(C=C)$_n$CON($R^6$)—, n is preferably 1 or 2, and $R^6$ is preferably hydrogen atom. When X represents —N($R^7$)CON($R^8$)—, $R^7$ and $R^8$ are preferably hydrogen atoms. When X represents —SO$_2$N($R^9$)—, $R^9$ is preferably hydrogen atom. When X represents —N($R^{10}$)—, $R^{10}$ is preferably hydrogen atom or a $C_{1-6}$ alkyl group, more preferably hydrogen atom or methyl group. When X represents a $C_{1-6}$ alkylene group, the alkylene group may be linear or branched. When this alkylene group contains an unsaturated bond, the unsaturated bond may be either a double bond or a triple bond, or a combination of the both. The alkylene group preferably contains one triple bond.

When X represents an aryldiyl group, the aryl ring constituting the aryldiyl group may be either a monocyclic aryl ring or a condensed aryl ring, and an aryldiyl group comprising a 6- to 14-membered aryl ring can be used. More specifically, examples of the aryldiyl group include, for example, phenylene group, naphthyldiyl group, anthryldiyl group and the like.

When X represents a heterocyclic diyl group, the heterocyclic ring constituting the heterocyclic diyl group may be a monocyclic heterocyclic group or a condensed heterocyclic group. A 5- or 6-membered monocyclic heterocyclic ring is preferred. The heterocyclic ring may be any of saturated, partially saturated and aromatic heterocyclic rings. Type and number of heteroatoms contained in the heterocyclic ring are not particularly limited. A heterocyclic group preferably contains one or more heteroatoms selected from the group consisting of nitrogen atom, oxygen atom and sulfur atom as ring-constituting atoms. When two or more heteroatoms are contained, they may be identical or different. Examples of heterocyclic ring constituting the heterocyclic diyl group include pyrrolidinediyl group, piperazinediyl group, morpholinediyl group, tetrahydrofurandiyl group, dihydropyrandiyl group, pyridinediyl group, pyrimidinediyl group, pyrazinediyl group, pyridazinediyl group, triazinediyl group, quinolinediyl group, isoquinolinediyl group, quinazolinediyl group, phthalazinediyl group, quinoxalinediyl group, naphthylidinediyl group, cinnolinediyl group, thiophenediyl group, furandiyl group, pyrrolediyl group, pyrrolinediyl group, imidazolediyl group, pyrazolediyl group, triazolediyl group, tetrazolediyl group, oxazolediyl group, thiazolediyl group, thiadiazolediyl group, benzothiophenediyl group, benzofurandiyl group, indolediyl group, indazolediyl group, benzimidazolediyl group, benzotriazolediyl group, benzoxazolediyl group, benzothiazolediyl group, purinediyl group and the like.

When Y represents —OR$^{11}$, $R^{11}$ is preferably hydrogen atom or a $C_{1-6}$ alkyl group, more preferably hydrogen atom or methyl group. When Y represents —NHR$^{12}$, $R^{12}$ is preferably amino group. In the aforementioned general formula (I), $R^4$ is preferably hydrogen atom or a $C_{1-6}$ alkyl group, and Y is preferably hydrogen atom, hydroxyl group, a $C_{1-6}$ alkoxyl group, hydrazino group or a halogen atom.

The compounds of the present invention represented by the general formula (I) may exist in the forms of acid addition salts or base addition salts, and any of such salts also fall within the scope of the compounds of the present invention. Examples of the acid addition salts include mineral acid salts such as hydrochloride or hydrobromide, and organic acid salts such as p-toluenesulfonate, methanesulfonate, oxalate, or tartrate. As the base addition salts, metal salts such as, for example, sodium salt, potassium salt, magnesium salt, or calcium salt, ammonium salts, or organic amine salts such as triethylamine salt or ethanolamine salt may be used. Further, the compounds may exist in the forms of amino acid salts such as glycine salt. Furthermore, the compounds of the present invention and salts thereof may also exist as hydrates or solvates, and these substances also fall within the scope of the present invention.

The compounds of the present invention may have one or more asymmetric carbon atoms depending on types of substituents. Any stereoisomers such as optical isomers and diastereomers, any mixtures of the stereoisomers, racemates and the like all fall within the scope of the present invention. Further, geometric isomers based on an olefinic double bond (syn- or anti-isomer) and any mixtures thereof as well as tautomers, if exist, also all fall within the scope of the present invention.

The following compounds are preferred compounds among the compounds of the present invention represented by the aforementioned general formula (I). However, the compounds of the present invention are not limited to these compounds.

TABLE 1

[Structure: Tp05 — tetramethyltetrahydronaphthalene linked to hydroxy-tropone]

Tp05

[Structure: tetramethyltetrahydronaphthalene-N(R10)-aryl-tropone with R1]

| | R¹ | R¹⁰ |
|---|---|---|
| Tp10 | H | H |
| Tp20 | Me | H |
| Tp22 | Me | Me |

[Structure: tetramethyltetrahydronaphthalene-X-tropone]

| | X |
|---|---|
| Tp30 | —NHCONH— |
| Tp40 | —SO₂NH— |
| Tp150 | —CH₂CH₂— |
| Tp180 | -para-Ph— |
| Tp190 | -meta-Ph— |

[Structure: tetramethyltetrahydronaphthalene-C(O)N(R⁵)-tropone with R¹]

| | R¹ | R⁵ |
|---|---|---|
| Tp80 | H | H |
| Tp82 | H | Me |
| Tp84 | Me | H |

[Structure: 3,5-disubstituted phenyl-X-tropone]

| | R | X |
|---|---|---|

TABLE 1-continued

| Tp50 | tert-Bu | —CONH— |
| Tp60 | CF₃ | —CONH— |
| Tp155 | tert-Bu | —C≡C— |
| Tp170 | tert-Bu | —N=N— |

[Structure: Tp88 — adamantyl-methoxyphenyl-CONH-tropone]

Tp88

[Structure: tetramethyltetrahydronaphthalene-(CH=CH)ₙ-C(O)NH-tropone with Y]

| | n | Y |
|---|---|---|
| Tp90 | 1 | OH |
| Tp93 | 1 | Cl |
| Tp95 | 2 | OH |

[Structure: tetramethyltetrahydronaphthalene-C≡C-tropone with R¹ and Y]

| | R¹ | Y |
|---|---|---|
| Tp140 | H | OH |
| Tp141 | H | OMe |
| Tp145 | Me | OH |
| Tp146 | H | NH₂NH₂ |
| Tp149 | H | H |

[Structure: tetramethyltetrahydronaphthalene-N=N-tropone with R⁴]

| | R⁴ |
|---|---|
| Tp160 | H |
| Tp175 | isoPr |

TABLE 1-continued

| | Z |
|---|---|
| Tp200 | O |
| Tp210 | S |

| | Z |
|---|---|
| Tp250 | —CH=CH— |
| Tp260 | S |

Methods for preparation of the aforementioned preferred compounds encompasses within the compounds of the formula (I) are specifically described in the examples given in the present specification. Therefore, any compounds falling within the scope of the present invention can be prepared by suitably selecting starting materials, regents, reaction conditions and the like used in those preparation methods, and if necessary, appropriately modifying or altering the preparation methods. However, the preparation methods of the compounds of the present invention are not limited to those specifically explained in the examples.

The compounds represented by the aforementioned general formula (I) and salts thereof have retinoid-like physiological activities (typical examples include cell differentiation activity, cell proliferation enhancing activity, life supporting activity and the like) and an action of controlling physiological activities of retinoids. Further, the compounds and salts thereof have an action of suppressing physiological activities of substances that bind to receptors belonging to the intranuclear receptor super family present in cellular nuclei to exhibit their physiological activities (e.g., steroid compounds, vitamin D compounds including vitamin $D_3$, thyroxine and the like). Further, they can also suppress actions of orphan receptors which exist in nuclei and whose ligands are unknown.

Therefore, the medicaments comprising the compounds represented by general formula (I) or physiologically acceptable salts thereof as active ingredients are useful as agents having retinoid-like activities. The medicaments of the present invention comprising the aforementioned compounds as active ingredients have, for example, cell differentiation activity, cell proliferation enhancing activity, life supporting activity and the like, and they can be used as active ingredients of medicaments for preventive or therapeutic treatments of vitamin A deficiency disease, hyperkeratosis of epithelial tissue, psoriasis, allergic diseases, immunological diseases such as rheumatism, bone diseases, diabetes mellitus, leukemia, or cancers.

The medicament of the present invention comprises, as an active ingredient, one or more kinds of substances selected from the group consisting of the compounds represented by the aforementioned general formula (I) and salts thereof, and hydrates thereof and solvates thereof. As the medicament of the present invention, the aforementioned substance, per se, may be administered. A pharmaceutical composition for oral administration or parenteral administration may preferably be administered which can be prepared by a method well known to those skilled in the art. Examples of the pharmaceutical compositions suitable for oral administrations include, for example, tablets, capsules, powders, subtilized granules, granules, liquids, syrups and the like. Examples of the pharmaceutical compositions suitable for parenteral administrations include, for example, injections, drops, suppositories, inhalants, eye drops, nasal drops, ointments, creams, patches, transdermal preparations, transmucosal preparations and the like.

Examples of pharmaceutically acceptable additives used for preparation of the aforementioned pharmaceutical compositions include, for example, excipients, disintegrators and disintegrating aids, binders, lubricants, coating agents, colorants, diluents, base materials, dissolving agents and dissolving aids, isotonic agents, pH modifiers, stabilizers, propellants, adhesives and the like. They can be suitably selected by those skilled in the art depending on the form of the pharmaceutical composition, and two or more kinds of them may be used in combination. The aforementioned pharmaceutical composition may be further added with one or more kinds of active ingredients such as retinoids and steroid compounds and used as a pharmaceutical composition in the form of so-called combined medicament. The pharmaceutical composition can be prepared in the form either for oral administration or parenteral administration.

EXAMPLES

The present invention will be more specifically explained with reference to the following examples. However, the scope of the present invention is not limited to these examples. The compound numbers in the examples correspond to those of the compounds described above as preferred examples.

Example 1

Synthesis of Compound Tp05

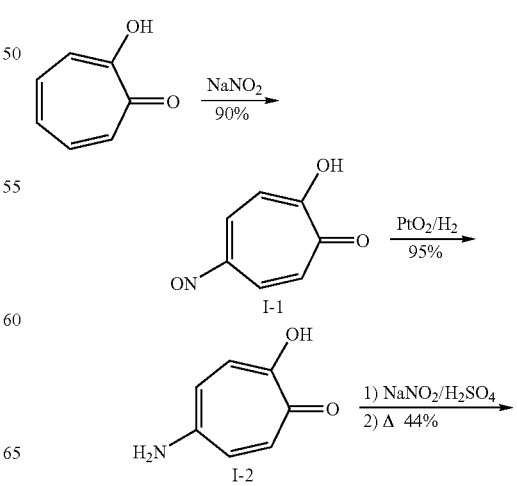

-continued

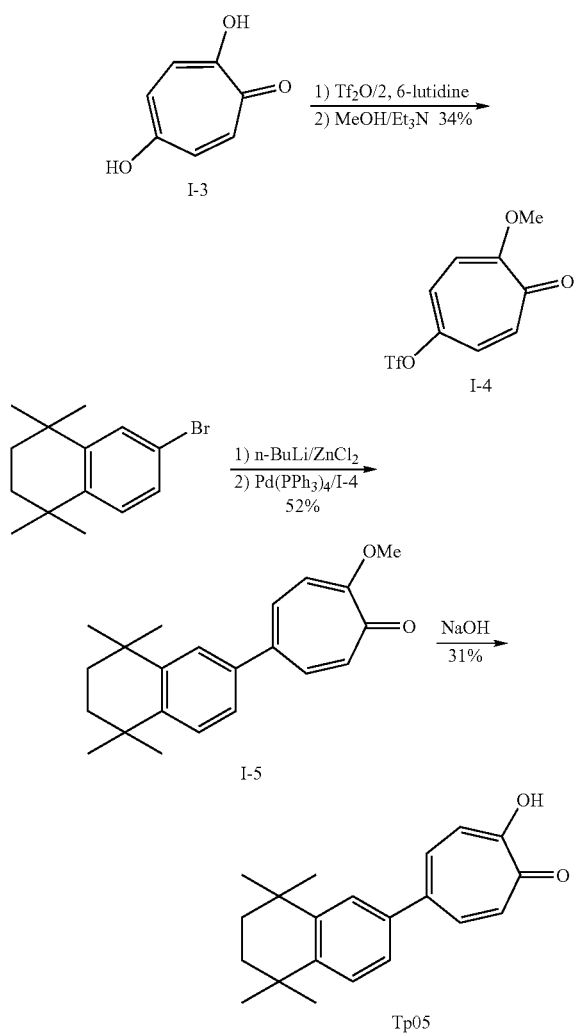

Tropolone (4.54 g, 37.2 mmol) was dissolved in acetic acid (12 ml) and water (4 ml) and gradually added with sodium nitrite (3.72 g, 53.9 mmol) dissolved in water (8 ml) under ice cooling. After 1 hour, the reaction solution was added with water, and the crystals were collected by filtration, then sufficiently washed with water, washed with a small amount of methanol and dried to obtain a crude product of Compound I-1 (5.03 g, 90%). Compound I-1: $^1$H-NMR (400 MHz, DMSO-$d_6$, 30° C.) 13.92 (s, 1H), 7.70 (d, J=12.4 Hz, 1H), 7.22 (d, J=11.7 Hz, 1H), 6.56 (d, J=12.8 Hz, 2H)

Compound I-1 (5.00 g, 33.1 mmol) was suspended in methanol (50 ml) and added with $PtO_2$ (40 mg) to perform catalytic hydrogen reduction. After 2.5 hours, the reaction was terminated, and the reaction solution was added with activated carbon (500 mg) and filtered through Cerite, and the filtrate was concentrated to obtain a crude product of Compound I-2 (4.30 g, 95%). Compound I-2: $^1$H-NMR (400 MHz, DMSO-$d_6$, 30° C.) 7.10 (dd, J=10.6, 1.3 Hz, 2H), 6.71 (dd, J=10.6, 1.3 Hz, 2H), 6.23 (s, 2H)

Compound I-2 (1.99 g, 14.5 mmol) was suspended in water (50 ml) and concentrated sulfuric acid (22.4 ml) and gradually added with a solution of sodium nitrite (1.20 g, 17.4 mmol) dissolved in water (5 ml). After stirring for 30 minutes, the reaction solution was refluxed for 2 hours. Then, the reaction solution was cooled, added with water and extracted with ethyl acetate, and the organic layer was washed with saturated brine, dehydrated over $MgSO_4$ and then concentrated to obtain a crude product of Compound I-3 (836 mg, 42%). Compound I-3: $^1$H-NMR (400 MHz, DMSO-$d_6$, 30° C.) 10.24 (b, 1H), 7.15 (dt, J=11.7, 1.3 Hz, 2H), 6.96 (dd, J=10.4, 1.5 Hz, 2H)

Compound I-3 (420 mg, 3.04 mmol) and 2,6-lutidine (0.85 ml, 782 mg, 7.30 mmol, 2.4 Eq) was suspended in methylene chloride (5 ml), added with trifluoroacetic anhydride (TFA) (1.89 g, 6.70 mmol) at −30° C. and stirred at room temperature. After 3.5 hours, the reaction solution was added with water and extracted with methylene chloride, and the organic layer was washed with 2 N hydrochloric acid and saturated brine, dehydrated over $MgSO_4$, and then concentrated. The total crude crystals were dissolved in methanol (5 ml), added with triethylamine (1 ml) and stirred at room temperature. After 3 hours, the solvent was evaporated, and the residue was purified by silica gel column chromatography (ethyl acetate), to obtain Compound I-4 (258 mg, 34%). Compound I-4: $^1$H-NMR (400 MHz, DMSO-$d_6$, 30° C.) 7.45 (dd, J=12.9, 2.9 Hz, 1H), 7.39 (dd, J=10.7, 2.9 Hz, 1H), 7.10 (d, J=12.9 Hz, 1H), 6.93 (d, J=10.7 Hz, 1H), 3.90 (s, 3H)

2-Bromo-5,6,7,8-tetrahydro-5,5,8,8-tetramethylnaphthalene (328 mg, 1.23 mmol) was dissolved in tetrahydrofuran (THF, 3 ml), added with a 1.6 M solution of n-BuLi (1.48 mmol) in hexane (0.92 ml) at −78° C. and stirred for 30 minutes. This solution was added to a solution of zinc chloride (168 mg, 1.23 mmol) dissolved in THF (2 ml) and stirred at room temperature. After 1 hour, the reaction solution was added to a solution of Compound I-4 (220 mg, 0.82 mmol) and $Pd(PPh_3)_4$ (71 mg, 0.062 mmol) dissolved in THF (5 ml) and stirred at room temperature. After 4 hours, the reaction solution was added with water and extracted with ethyl acetate, and the organic layer was washed with saturated brine, dehydrated over $MgSO_4$ and then concentrated. The residue was purified by flash silica gel column chromatography (ethyl acetate:n-hexane=2:1) to obtain Compound I-5 (138 mg, 52%). Compound I-5: $^1$H-NMR (400 MHz, DMSO-$d_6$, 30° C.) 7.55 (dd, 1H, overlapped with $Pd(PPh_3)_4$), 7.47 (d, J=2.2 Hz, 1H), 7.40 (d, J=8.3 Hz, 1H), 7.37 (dd, J=10.3, 1.7 Hz, 1H), 7.30 (dd, J=8.1, 2.0 Hz, 1H), 7.11 (d, J=12.7 Hz, 1H), 7.07 (d, J=10.5 Hz, 1H), 7.07 (d, J=10.5 Hz, 1H), 3.87 (s, 4H), 1.66 (s, 4H), 1.29 (s, 6H), 1.26 (s, 6H)

Compound I-5 (130 mg, 0.40 mmol) was dissolved in ethanol (6 ml), added with 2 N sodium hydroxide (3 ml) and stirred at room temperature. After 15 hours, the reaction solution was made acidic with 2 N hydrochloric acid, extracted with ethyl acetate, washed with saturated brine, dehydrated over $MgSO_4$ and then concentrated. The residue was recrystallized from ethanol to obtain Compound Tp05 (38 mg, 31%). Compound Tp05: yellow needle crystals (ethanol); melting point 161° C.; $^1$H-NMR (400 MHz, DMSO-$d_6$, 30° C.) 7.64 (d, J=11.7 Hz, 2H), 4.78 (d, J=2.0 Hz, 1H), 7.40 (d, J=8.3 Hz, 1H), 7.30 (dd, J=8.3, 2.0 Hz, 1H), 7.27 (d, J=11.7 Hz, 2H); Anal. Calcd. for $C_{21}H_{24}O_2$ C, (81.78%); H, (7.87%); Found C, (81.57%); H, (7.87%);

Example 2

Synthesis of Compound Tp10

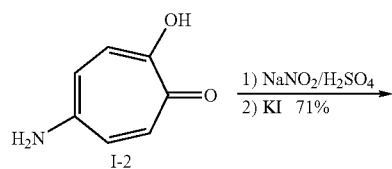

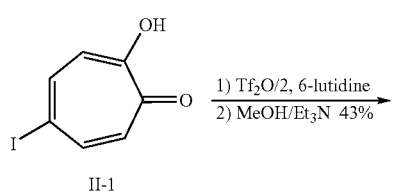

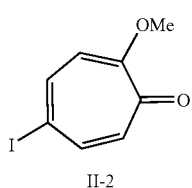

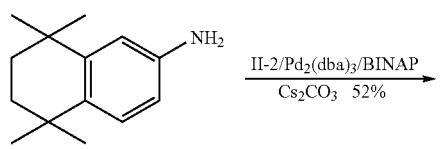

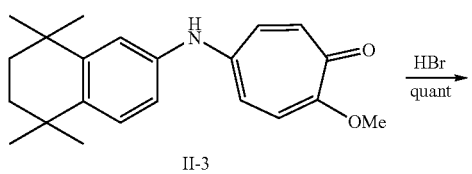

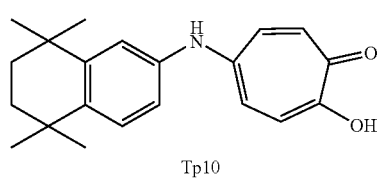

Compound I-2 (5.38 g, 39.3 mmol) was suspended in concentrated hydrochloric acid (21 ml) and added with ice (30 g). The reaction solution was gradually added with sodium nitrite (2.98 g, 43.2 mmol) dissolved in water (15 ml) at 0° C. and stirred for further 30 minutes. The reaction solution was returned to room temperature and gradually added with a solution of potassium iodide (71.7 g, 432 mmol) dissolved in water (90 ml) and the mixture was left with stirring overnight. The reaction solution was added with ethyl acetate, and the insoluble solids were removed by filtration to obtain a crude product of Compound II-1 (3.45 g). The ethyl acetate layer was further washed with saturated brine, dehydrated over $MgSO_4$ and then concentrated to obtain Compound II-1 (3.45 g, 6.90 g in total, 71%). Compound II-1: $^1$H-NMR (400 MHz, DMSO-$d_6$, 30° C.) 7.83 (d, J=11.9 Hz, 2H), 6.81 (d, J=11.7 Hz, 2H)

Compound II-1 (300 mg, 1.21 mmol) and 2,6-lutidine (0.11 ml, 97 mg, 1.45 mmol, 2.4 Eq) were suspended in methylene chloride (3 ml), added with anhydrous TFA (375 mg, 1.33 mmol) −30° C. and stirred at room temperature. After 2 hours, the reaction solution was added with water and extracted with methylene chloride, and the organic layer was washed with 2 N hydrochloric acid and saturated brine, dehydrated over $MgSO_4$ and then concentrated. The total crude crystals were dissolved in methanol (4 ml), added with triethylamine (1.5 ml) and stirred at room temperature. After 1 hour, the solvent was evaporated, and the residue was purified by flash silica gel column chromatography (ethyl acetate:n-hexane=2:1) to obtain Compound II-2 (135 mg, 43%). Compound II-2: $^1$H-NMR (400 MHz, DMSO-$d_6$, 30° C.) 7.75 (dd, J=10.3, 1.7 Hz, 1H), 7.63 (dd, J=12.7, 1.7 Hz, 1H), 6.65 (d, J=12.7 Hz, 1H), 6.60 (d, J=1.5 Hz, 1H), 3.81 (s, 3H)

Compound II-2 (310 mg, 1.18 mmol), 2-amino-5,6,7,8-tetrahydro-5,5,8,8-tetramethylnaphthalene (240 mg, 1.18 mmol), cesium carbonate (463 mg, 1.42 mmol) and 2.5 mol % $Pd_2(dba)_3$ (27.1 mg, 0.030 mmol) and racemic BINAP (81.0 mg, 0.13 mmol) were suspended in anhydrous toluene (8 ml) and stirred at 100° C. After 5 hours, the reaction solution was cooled to room temperature, added with water and extracted with ethyl acetate, and the organic layer was washed with saturated brine, dehydrated over $MgSO_4$ and then concentrated. The residue was purified by flash silica gel column chromatography (ethyl acetate:methanol=40:1) to obtain Compound II-3 (98 mg, 19%). Compound II-3: $^1$H-NMR (400 MHz, DMSO-$d_6$, 30° C.) 8.51 (s, 1H), 7.27 (d, J=8.5 Hz, 1H), 7.15 (dd, J=13.2, 2.7 Hz, 1H), 7.02 (d, J=13.0 Hz, 1H), 6.94 (dd, J=8.5, 2.2 Hz, 1H), 6.93 (d, J=11.5 Hz, 1H), 6.55 (dd, J=11.2, 2.7 Hz, 1H), 3.71 (s, 3H), 1.64 (s, 4H), 1.24 (s, 12H)

Compound II-3 (90 mg, 0.27 mmol) was suspended in 47% HBr (5 ml) and refluxed. After 9 hours, the reaction solution was diluted with water and extracted with ethyl acetate, and the organic layer was washed with saturated brine, dehydrated over $MgSO_4$ and then concentrated. A crude product of Compound Tp10 was obtained (94 mg, quant). Compound Tp10: brown needle crystals (ethanol/water); melting point 216° C.; $^1$H-NMR (400 MHz, DMSO-$d_6$, 30° C.) 8.58 (s, 1H), 7.28 (d, J=8.3 Hz, 1H), 7.16 (dd, J=12.2, 2H), 7.03 (d, J=11.5 Hz, 2H), 7.02 (d, J=2.5 Hz, 1H), 6.94 (dd, J=8.5, 2.5 Hz, 1H), 1.64 (s, 4H), 1.23 (s, 6H), 1.23 (s, 6H)

Example 3

Synthesis of Compounds Tp20 and Tp22

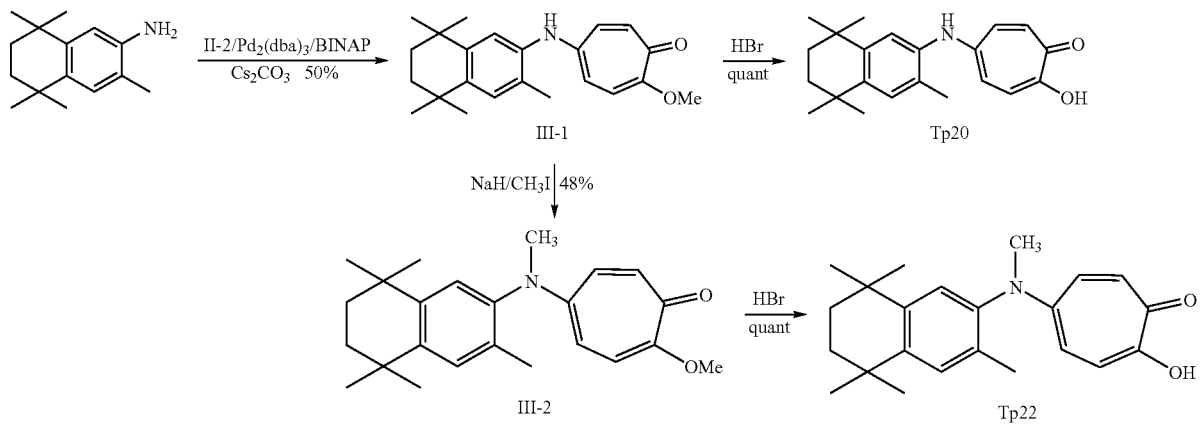

Compound II-2 (158 mg, 0.60 mmol), 2-amino-5,6,7,8-tetrahydro-3,5,5,8,8-tetramethylnaphthalene (131 mg, 0.60 mmol), cesium carbonate (236 mg, 0.72 mmol), 2.5 mol % $Pd_2(dba)_3$ (13.8 mg, 0.015 mmol) and racemic BINAP (41.1 mg, 0.066 mmol) were suspended in anhydrous toluene (4 ml) and stirred at 100° C. After 5 hours, the reaction solution was cooled to room temperature and added with water and extracted with ethyl acetate, and the organic layer was washed with saturated brine, dehydrated over $MgSO_4$ and then concentrated. The residue was purified by flash silica gel column chromatography (ethyl acetate:methanol=40:1) to obtain Compound III-1 (129 mg, 50%). Compound III-1: $^1$H-NMR (400 MHz, DMSO-$d_6$, 30° C.) 8.14 (s, 1H), 7.21 (s, 1H), 7.11 (dd, J=13.2, 2.2 Hz, 1H), 7.02 (s, 1H), 7.01 (d, J=13.0 Hz, 1H), 6.91 (d, J=11.2 Hz, 1H), 5.91 (dd, J=11.2, 2.4 Hz, 1H), 3.66 (s, 3H), 2.09 (s, 3H), 1.63 (s, 4H), 1.24 (s, 6H), 1.20 (s, 6H)

Compound III-1 (125 mg, 0.36 mmol) was suspended in 47% HBr (6 ml) and refluxed. After 3 days, the reaction solution was diluted with water and extracted with ethyl acetate, and the organic layer was washed with saturated brine, dehydrated over $MgSO_4$ and then concentrated. A crude product of Compound Tp20 was obtained (131 mg, quant). Compound Tp20: yellow powder (methylene chloride/n-hexane); melting point 166° C.; $^1$H-NMR (400 MHz, DMSO-$d_6$, 30° C.) 8.28 (s, 1H), 7.21 (s, 1H), 7.15 (d, J=12.2 Hz, 2H), 7.04 (s, 1H), 6.72 (d, J=12.2 Hz, 2H), 2.09 (s, 1H), 1.63 (s, 4H), 1.25 (s, 6H), 1.30 (s, 6H); Anal. Calcd. for $C_{22}H_{27}NO_2 \cdot 1/4H_2O$ C, (77.27%); H, (8.11%); N, (4.10%); Found C, (77.37%); H, (8.02%); N, (4.12%);

NaH (60% in oil, 16 mg, 0.43 mmol) was washed with n-hexane, dried and then suspended in DMF (1 ml). The suspension was added with Compound III-1 (100 mg, 0.28 mmol) dissolved in DMF (2 ml) and stirred at room temperature. After 20 minutes, the reaction solution was added with methyl iodide (0.1 ml) and stirred at room temperature for 1 hour. The reaction solution was added with water and extracted with ether, and the organic layer was washed with saturated brine, dehydrated over $MgSO_4$ and then concentrated. The residue was purified by flash silica gel column chromatography (ethyl acetate:methanol=40:1→20:1) to obtain Compound III-2 (70 mg, 48%). Compound III-2: $^1$H-NMR (400 MHz, DMSO-$d_6$, 30° C.) 7.28 (s, 1H), 7.03 (s, 1H), 7.01 (d, J=11.3 Hz, 1H), 6.89 (d, J=13.4 Hz, 1H), 6.72 (dd, J=13.4, 2.9 Hz, 1H), 6.22 (dd, J=11.3, 2.9 Hz, 1H), 3.72 (s, 3H), 3.18 (s, 3H), 2.04 (s, 3H), 1.63 (s, 4H), 1.26 (s, 6H), 1.19 (s, 6H)

Compound III-2 (65 mg, 0.18 mmol) was suspended in 47% HBr (3.5 ml) and refluxed. After 24 hours, the reaction solution was diluted with water and extracted with ethyl acetate, and the organic layer was washed with saturated brine, dehydrated over $MgSO_4$ and then concentrated. A crude product of Compound Tp22 was obtained (66 mg, quant). Compound Tp22: brown needle crystals (ethanol/water); melting point 168° C.; $^1$H-NMR (400 MHz, DMSO-$d_6$, 30° C.) 7.29 (s, 1H), 7.14 (d, J=12.4 Hz, 2H), 7.05 (s, 1H), 6.65 (d, J=12.5 Hz, 2H), 3.19 (s, 1H), 2.03 (s, 3H), 1.64 (s, 4H), 1.26 (s, 6H), 1.19 (s, 6H); Anal. Calcd. for $C_{23}H_{29}N_1O_2$ C, (78.60%); H, (8.32%); N, (3.98%); Found C, (78.47%); H, (8.41%); N, (3.92%);

Example 4

Synthesis of Compound Tp30

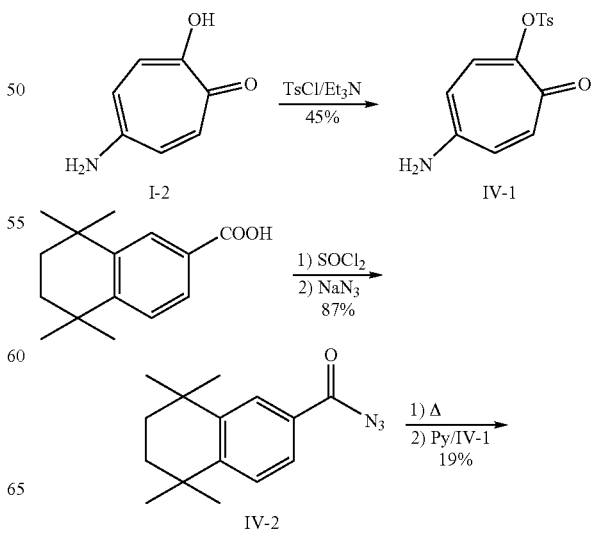

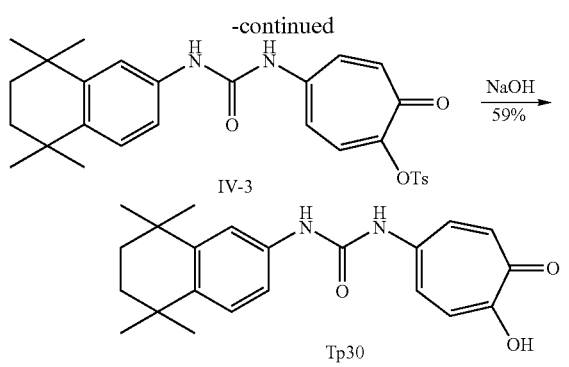

Compound I-2 (250 mg, 2.07 mmol) was suspended in anhydrous methylene chloride (5 ml), added with tosyl chloride (473 mg, 2.48 mmol) and triethylamine (1 ml) and stirred at room temperature. After 5 hours, the reaction solution was added with water and extracted with ethyl acetate, and the organic layer was washed with saturated brine, dehydrated over MgSO$_4$ and then concentrated. The residue was purified by flash silica gel column chromatography (ethyl acetate) to obtain Compound IV-1 (245 mg, 46%). $^1$H-NMR (400 MHz, DMSO-d$_6$, 30° C.) 7.77 (d, J=8.3 Hz, 2H), 7.41 (d, J=8.5 Hz, 2H), 7.22 (s, 2H), 7.05 (d, J=11.2 Hz, 1H), 6.98 (d, J=13.2 Hz, 1H), 6.96 (dd, J=13.4, 1.7 Hz, 1H), 5.92 (dd, J=11.2, 2.0 Hz, 1H), 2.40 (s, 3H)

5,6,7,8-Tetrahydro-5,5,8,8-tetramethylnaphthalene-2-carboxylic acid (500 mg, 2.16 mmol) was suspended in anhydrous benzene (5 ml) and thionyl chloride (2.56 g) and refluxed. After 2 hours, the solvent was evaporated, and the residue was dissolved in acetone (5 ml), added with sodium azide (238 mg, 3.66 mmol) dissolved in water (1.2 ml) and stirred at 35 to 40° C. for 30 minutes. The reaction solution was added with water, and the precipitates were collected by filtration and sufficiently washed with water. A crude product of Compound IV-2 was obtained (482 mg, 87%). Compound IV-2: $^1$H-NMR (400 MHz, DMSO-d$_6$, 30° C.) 7.89 (d, J=2.0 Hz, 1H), 7.68 (dd, J=8.3, 2.0 Hz, 1H), 7.51 (d, J=8.3 Hz, 1H), 1.66 (s, 4H), 1.25 (s, 12H)

Compound IV-2 (206 mg, 0.80 mmol) was suspended in anhydrous toluene (3 ml) and refluxed. After 2 hours, the reaction solution was returned to room temperature, added with Compound IV-1 (200 mg, 0.69 mmol) and dimethylaminopyridine (DMAP, 8.9 mg, 0.072 mmol) and refluxed. After 20 hours, the reaction solution was returned to room temperature, added with water and extracted with ethyl acetate, and after the insoluble solids were removed by filtration, the organic layer was washed with saturated brine, dehydrated over MgSO$_4$ and then concentrated. The residue was purified by silica gel column chromatography (ethyl acetate) to obtain Compound IV-3 (68 mg, 19%). Compound IV-3: $^1$H-NMR (400 MHz, DMSO-d$_6$, 30° C.) 9.27 (s, 1H), 8.81 (s, 1H), 7.80 (d, J=8.1 Hz, 2H), 7.50 (dd, J=11.7, 1.9 Hz, 1H), 7.45 (d, J=8.5 Hz, 2H), 7.38 (d, J=1.9 Hz, 1H), 7.37 (dd, J=16.8, 2.5 Hz, 1H), 7.34 (d, J=11.2 Hz, 1H), 7.23 (d, J=12.6 Hz, 1H), 7.16 (dd, J=8.3, 1.9 Hz, 1H), 7.14 (d, J=13.2 Hz, 1H), 2.42 (s, 3H), 1.62 (s, 3H), 1.22 (s, 6H), 1.21 (s, 6H)

Compound IV-3 (60 mg, 0.12 mmol) and sodium hydroxide (40 mg) were dissolved in methanol (12 ml) and stirred at room temperature. After 5 hours, the reaction solution was concentrated under reduced pressure at a temperature below 60° C., added with water, and after pH was made about 4.5 to 5.0 with 2 N hydrochloric acid, extracted with ethyl acetate, and the organic layer was washed with water and saturated brine, dehydrated over MgSO$_4$ and then concentrated. The residue was purified by flash silica gel column chromatography (ethyl acetate) to obtain Compound Tp30 (25 mg, 59%). Compound Tp30: light yellow powder (methanol); melting point 207° C.; $^1$H-NMR (400 MHz, DMSO-d$_6$, 30° C.) 8.78 (s, 1H), 8.59 (s, 1H), 7.57 (d, J=12.2 Hz, 2H), 7.37 (d, J=2.2 Hz, 1H), 7.22 (d, J=12.2 Hz, 2H), 7.20 (d, J=8.6 Hz, 1H), 7.15 (dd, J=2.2, 8.6 Hz, 1H), 1.62 (s, 4H), 1.22 (s, 6H), 1.21 (s, 6H); Anal. Calcd. for C$_{22}$H$_{26}$N$_2$O$_3$.1/2H$_2$O C, (70.38%); H, (7.25%); N, (7.46%); Found C, (70.32%); H, (7.21%); N, (7.37%);

Example 5

Synthesis of Compound Tp40

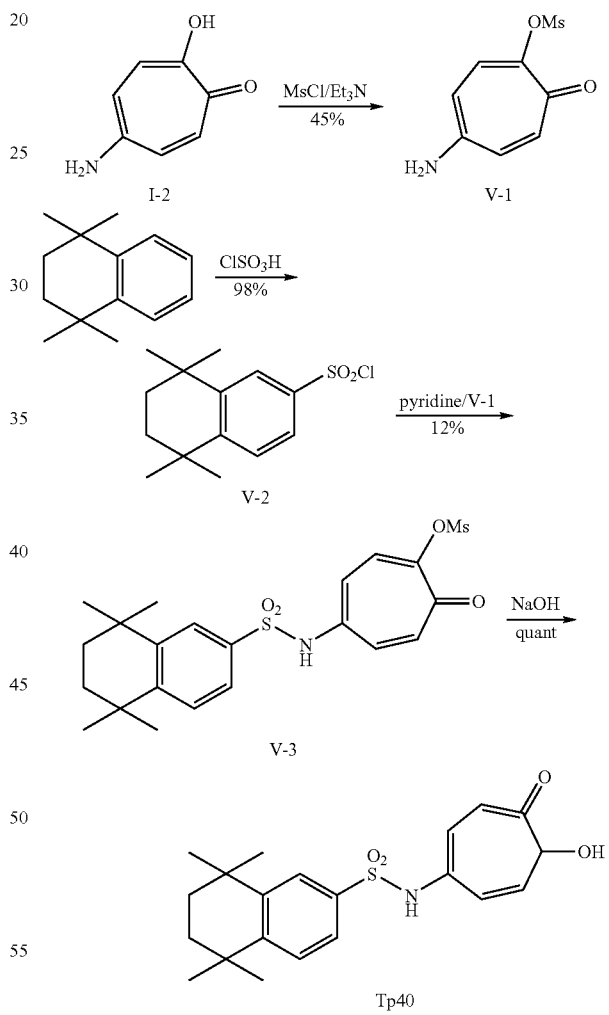

Compound I-2 (1.00 g, 7.30 mmol) was suspended in anhydrous methylene chloride (10 ml), added with triethylamine (1.5 ml) and mesyl chloride (836 mg, 0.56 ml, 7.30 mmol) and stirred at room temperature. After 28 hours, the solvent was evaporated, and the residue was purified by flash silica gel column chromatography (ethyl acetate) to obtain Compound V-1 (828 mg, 52%). Compound V-1: $^1$H-NMR (400 MHz, DMSO-d$_6$, 30° C.) 7.29 (bs, 2H), 7.24 (dd, J=12.2, 1.0 Hz, 1H), 7.13 (d, J=13.2 Hz, 1H), 7.02 (dd, J=13.2, 2.0 Hz, 1H), 6.02 (dd, J=11.7, 2.0 Hz, 1H), 3.33 (s, 3H)

Chlorosulfonic acid (2.0 ml) was added with 1,2,3,4-tetrahydro-1,1,4,4-tetramethylnaphthalene (1.00 g, 5.32 mmol) at 0° C. and stirred for about 1 hour. The reaction solution was poured into ice water and extracted with ether, and the organic layer was washed with saturated brine, dehydrated over MgSO$_4$ and then concentrated. A crude product of Compound V-2 was obtained (1.50 g, 98%). Compound V-2: $^1$H-NMR (400 MHz, CDCL$_3$) 7.93 (d, J=2.2 Hz, 1H), 7.74 (dd, J=8.6, 2.2 Hz, 1H), 7.52 (d, J=8.6 Hz, 1H), 1.73 (s, 4H), 1.33 (s, 6H), 1.32 (s, 6H)

Compound V-1 (200 mg, 0.93 mmol) and Compound V-2 (267 mg, 0.93 mmol) were suspended in anhydrous pyridine (3 ml) and stirred at room temperature. After 2 hours, the reaction solution was added with water and extracted with ethyl acetate, and the organic layer was washed with 2 N hydrochloric acid and saturated brine, dehydrated over MgSO$_4$ and then concentrated. The residue was purified by silica gel column chromatography (ethyl acetate) to obtain Compound V-3 (50 mg, 12%). Compound V-3: $^1$H-NMR (400 MHz, DMSO-d$_6$, 30° C.) 10.94 (b, 1H), 7.73 (s, 1H), 7.58 (s, 2H), 7.51 (d, J=10.7 Hz, 1H), 7.30 (dd, J=13.5, 2.7 Hz, 1H), 7.21 (d, J=13.2 Hz, 1H), 6.89 (dd, J=10.9, 2.7 Hz, 1H), 3.42 (s, 3H), 1.63 (s, 4H), 1.22 (s, 6H), 1.20 (s, 6H)

Compound V-3 (45 mg, 0.097 mmol) was dissolved in ethanol (3 ml) and 2 N sodium hydroxide (1 ml) and stirred at room temperature. After 6 hours, the reaction solution was made acidic with 2 N hydrochloric acid and extracted with ethyl acetate, and the organic layer was washed with saturated brine, dehydrated over MgSO$_4$ and then concentrated. A crude product of Compound Tp40 was obtained (39 mg, quant). Compound Tp40: light yellow prisms (ethyl acetate/n-hexane); melting point 211° C.; $^1$H-NMR (400 MHz, DMSO-d$_6$, 30° C.) 10.11 (s, 1H), 7.53 (d, J=2.2 Hz, 1H), 7.51 (d, J=8.3 Hz, 1H), 7.44 (dd, J=8.3, 2.0 Hz, 1H), 7.13 (d, J=12.2 Hz, 2H), 7.19 (d, J=12.5 Hz, 2H), 1.61 (s, 4H), 1.21 (s, 6H), 1.13 (s, 6H); Anal. Calcd. for C$_{21}$H$_{25}$N$_1$O$_4$S$_1$ C, (65.09%); H, (6.50%); N, (3.61%); Found C, (64.84%); H, (6.47%); N, (3.69);

Example 6

Synthesis of Compound Tp50

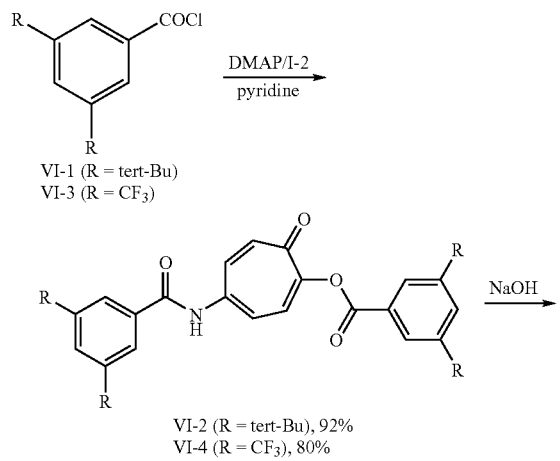

VI-2 (R = tert-Bu), 92%
VI-4 (R = CF$_3$), 80%

-continued

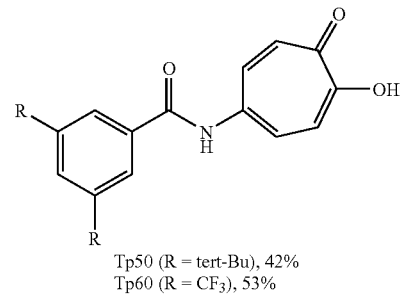

Tp50 (R = tert-Bu), 42%
Tp60 (R = CF$_3$), 53%

Acid chloride VI-1 prepared from 3,5-di-t-butylbenzoic acid (550 mg, 2.00 mmol) was added with Compound I-2 (158 mg, 1.15 mmol), pyridine (10 ml) and one piece of DMAP. After the starting materials disappeared, the reaction solution was poured into 2 N hydrochloric acid and extracted with methylene chloride, and the organic layer was dried over sodium sulfate. Then, the solvent was evaporated, and the residue was purified by flash silica gel column chromatography (n-hexane:ethyl acetate=2:1) to obtain Compound VI-2 (600 mg, 92%).

Compound V-2 (600 mg, 1.05 mmol) was dissolved in ethanol (10 ml), added with 5% sodium hydroxide (10 ml) and stirred. After the starting materials disappeared, the reaction solution was poured into 2 N hydrochloric acid (30 ml), made pH 2 and extracted with ethyl acetate. The organic layer was dried over sodium sulfate, and the solvent was evaporated. The residue was purified by ODS flash column chromatography (acetonitrile:water=2:1) to obtain Compound Tp50 (149 mg, 42%). Compound Tp50: light yellow prisms (methylene chloride/n-hexane); melting point 236° C.; Anal. Calcd. for C$_{22}$H$_{27}$N$_1$O$_3$ C, (74.76%); H, (7.70%); N, (3.96%); Found C, (74.56%); H, (7.63%); N, (3.82%);

Example 7

Synthesis of Compound Tp60

3,5-Bistrifluoromethylbenzoyl chloride (Compound VI-3, 560 mg, 2.02 mmol), Compound I-2 (137 mg, 1.00 mmol), pyridine (5 ml) and one piece of DMAP were added. After the starting materials disappeared, the reaction solution was poured into 2 N hydrochloric acid and extracted with methylene chloride. The organic layer was dried over sodium sulfate, and then the solvent was evaporated. The residue was purified by flash silica gel column chromatography (n-hexane:ethyl acetate=2:1) to obtain Compound VI-4 (500 mg, 80%). Compound VI-4: $^1$H-NMR (400 MHz, CDCl$_3$) 9.00 (S, 1H), 8.47 (s, 2H), 8.39 (s, 2H), 8.12 (s, 1H), 8.03 (s, 1H), 7.70 (d, J=12.1 Hz, 2H), 7.35 (d, J=12.1 Hz, 2H)

Compound VI-4 (500 mg, 0.81 mmol) was dissolved in ethanol (6 ml), added with 5% sodium hydroxide (3 ml) and stirred. After the starting materials disappeared, the reaction solution was poured into 2 N hydrochloric acid (30 ml), made pH 2 and extracted with methylene chloride. The organic layer was dried over sodium sulfate, and then the solvent was evaporated. The residue was purified by ODS flash column chromatography (acetonitrile:water=1:1) to obtain Compound Tp60 (160 mg, 53%). Compound Tp60: light yellow prisms (methanol); melting point 149-150° C.; $^1$H-NMR (400 MHz, CDCl$_3$) 8.33 (s, 2H), 8.09 (s, 1H), 8.05 (s, 1H), 7.71 (d, J=11.3 Hz, 2H), 7.38 (d, J=11.5 Hz, 2H);

Anal. Calcd. for $C_{16}H_9N_1O_3F_6$ C, (50.94%); H, (2.40%); N, (3.71%); Found C, (50.87%); H, (2.70%); N, (3.44%);

Example 8

Synthesis of Compounds Tp80, Tp82 and Tp84

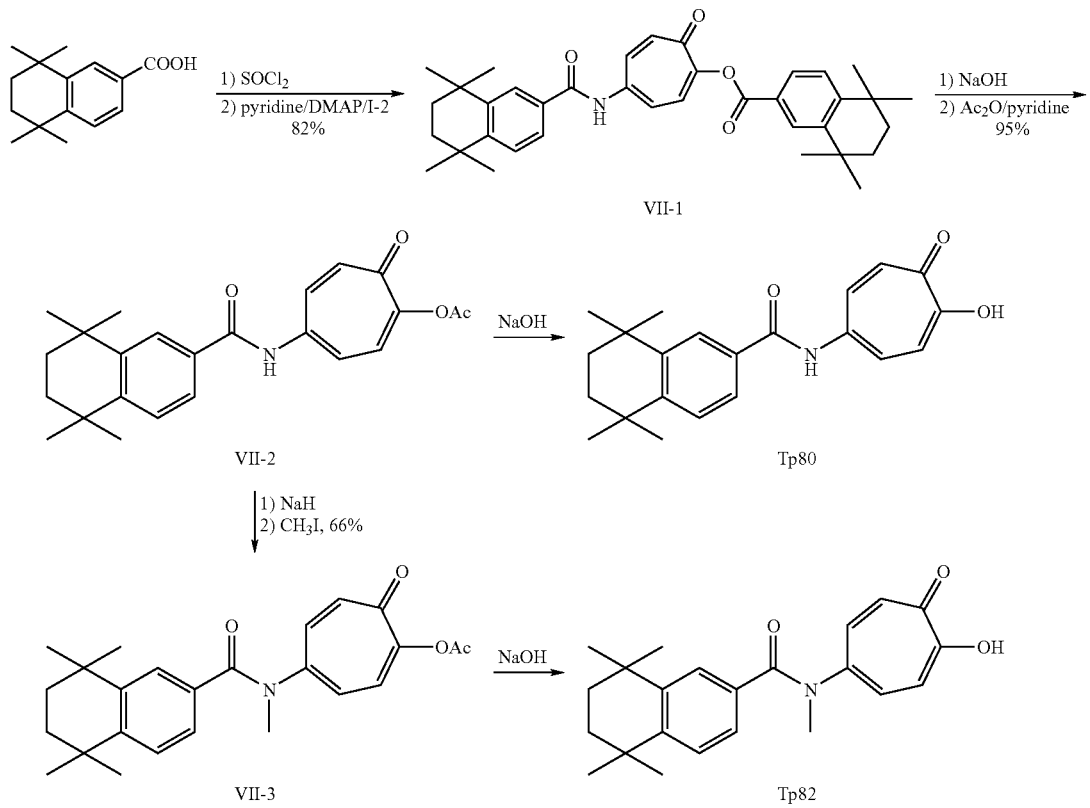

5,6,7,8-Tetrahydro-5,5,8,8-tetramethylnaphthalene-2-carboxylic acid (7.00 g, 30.2 mmol) was suspended in thionyl chloride (18.0 g) and anhydrous benzene (20 ml) and refluxed by heating. After 2 hours, the solvent was evaporated, and the residue was added with 5-aminotropolone (2.07 g, 15.1 mmol), suspended in anhydrous pyridine (20 ml), added with one piece of DMAP and stirred at 100° C. After 1 hour, the reaction solution was added with water and extracted with methylene chloride, and the organic layer was washed with 2 N hydrochloric acid and saturated brine, dehydrated over $MgSO_4$ and then concentrated. The residue was purified by silica gel column chromatography (ethyl acetate:methylene chloride=1:20) to obtain Compound VII-1 (6.96 g, 82%). Compound VII-1: $^1$H-NMR (400 MHz, $CDCl_3$) 8.13 (d, J=2.0 Hz, 1H), 7.98 (s, 1H), 7.90 (dd, J=8.3, 2.0 Hz, 1H), 7.86 (d, J=2.2 Hz, 1H), 7.56 (dd, J=8.3, 2.0 Hz, 1H), 7.41 (d, J=8.3 Hz, 1H), 7.40 (b, 1H), 7.38 (d, J=8.3 Hz, 1H), 7.29 (bd, J=11.7 Hz, 2H), 7.29 (b, 1H), 1.72 (s, 8H), 1.33 (s, 6H), 1.32 (s, 6H), 1.31 (s, 6H), 1.29 (s, 6H)

Compound VII-1 (6.96 g, 12.3 mmol) was dissolved in methylene chloride (40 ml) and ethanol (40 ml), added with 2 N sodium hydroxide (30 ml) and stirred at room temperature. After 20 hours, the reaction solution was made acidic with 2 N hydrochloric acid and extracted with ethyl acetate. The organic layer was washed with saturated brine, dried over $MgSO_4$ and then concentrated. A mixture of a crude product of Tp80 and 5,6,7,8-tetrahydro-5,5,8,8-tetramethyl-2-naphthoic acid (7.35 g in total, quant.) was obtained. This mixture (6.43 g) was dissolved in anhydrous pyridine (20 ml) and acetic anhydride (30 ml) and stirred at room temperature. After 2 hours, the solvent was evaporated under reduced pressure, and the residue was purified by flash silica gel column chromatography (ethyl acetate:methylene chloride=1:3) to obtain Compound VII-2 (4.12 g, 95%). Compound VII-2: $^1$H-NMR (400 MHz, $CDCl_3$) 7.87 (br s, 1H), 7.84 (d, J=2.0 Hz, 1H), 7.54 (dd, J=8.3, 2.0 Hz, 1H), 7.53 (b, 2H), 7.43 (d, J=8.3 Hz, 1H), 7.23 (d, J=12.0 Hz, 2H), 2.34 (s, 3H), 1.72 (s, 4H), 1.34 (s, 6H), 1.31 (s, 6H)

Compound VII-2 (4.12 g, 10.5 mmol) was dissolved in methylene chloride (50 ml) and ethanol (40 ml), added with 2 N sodium hydroxide (40 ml) and stirred at room temperature. After 2 hours, the reaction solution was made acidic with 2 N hydrochloric acid and extracted with ethyl acetate. The organic layer was washed with saturated brine, dehydrated over $MgSO_4$ and then concentrated to obtain a crude product of Tp80 (2.90 g, 91%). Tp80: light yellow scaly crystals (methanol); melting point 209° C.; $^1$H-NMR (400 MHz, $CDCl_3$) 7.83 (d, J=2.0 Hz, 1H), 7.73 (s, 1H), 7.71 (d, J=12.3 Hz, 2H), 7.54 (dd, J=8.2, 1.8 Hz, 1H), 7.42 (d, J=8.3 Hz, 1H), 7.36 (d, J=12.1 Hz, 2H), 1.72 (s, 4H), 1.33

(s, 6H), 1.31 (s, 6H); Anal. Calcd. for $C_{22}H_{25}NO_3$ C, (75.19%); H, (7.17%); N, (3.99%); Found C, (75.24%); H, (7.27%); N, (3.90%);

NaH (60%, 31 mg, 0.76 mmol) was washed with n-hexane and suspended in DMF (1 ml). The suspension was added with Compound VII-2 (200 mg, 0.51 mmol) dissolved in DMF (3 ml) and stirred at room temperature. After 15 minutes, the reaction solution was added with methyl iodide (0.1 ml) and stirred at room temperature. After 30 minutes, the reaction solution was added with water and extracted with methylene chloride. The organic layer was washed with saturated brine, dehydrated over $MgSO_4$ and then concentrated. The residue was purified by flash silica gel column chromatography (ethyl acetate:n-hexane=1:1) to obtain Compound VII-3 (136 mg, 66%). Compound VII-3: $^1$H-NMR (400 M Hz, DMSO-$d_6$, 30° C.) 7.32 (d, J=8.1 Hz, 1H), 7.26 (dd, J=8.1, 1.7 Hz, 1H), 7.16 (d, J=12.2 Hz, 2H), 7.13 (d, J=1.7 Hz, 1H), 7.10 (d, J=11.7 Hz, 2H), 3.35 (s, 3H), 1.55 (s, 4H), 1.18 (s, 6H), 1.01 (s, 6H)

Compound VII-3 (133 mg, 0.33 mmol) was dissolved in ethanol (8 ml), added with 2 N sodium hydroxide (4 ml) and stirred at room temperature. After 2 hours, the reaction solution was made acidic with 2 N hydrochloric acid and extracted with ethyl acetate. The organic layer was washed with saturated brine, dehydrated over $MgSO_4$ and then concentrated to obtain a crude product of Tp82 (120 mg, quant.). Tp82: light yellow scaly crystals (methylene chloride/n-hexane); melting point 194° C.; $^1$H-NMR (400 M Hz, DMSO-$d_6$, 30° C.) 7.28 (d, J=8.0 Hz, 1H), 7.27 (d, J=12.0 Hz, 1H), 7.20 (dd, J=9.0, 1.7 Hz, 1H), 7.07 (d, J=1.7 Hz, 1H), 7.01 (d, J=12.0 Hz, 2H), 3.32 (s, 3H), 1.53 (s, 4H), 1.16 (s, 6H), 0.97 (s, 6H); Anal. Calcd. for $C_{23}H_{27}N_1O_3$. 1/4$H_2O$ C, (74.67%); H, (7.49%); N, (3.78%); Found C, (74.91%); H, (7.58%); N, (3.71%);

5,6,7,8-Tetrahydro-3,5,5,8,8-pentamethylnaphthalene-2-carboxylic acid was used as a starting material to synthesize Compound Tp84 in the same manner as that used for Compound Tp80. Tp84: light yellow powdery crystals (methylene chloride/n-hexane); melting point 206° C.; $^1$H-NMR (400 MHz, $CDCl_3$) 7.72 (d, J=12.0 Hz, 2H), 7.45 (bs, 1H), 7.41 (s, 1H), 7.37 (d, J=12.0 Hz, 2H), 7.20 (s, 1H), 2.46 (s, 3H), 1.70 (s, 4H), 1.30 (s, 6H), 1.29 (s, 6H); Anal. Calcd. for $C_{23}H_{27}NO_3$ C, (75.59%); H, (7.45%); N, (3.83%); Found C, (75.49%); H, (7.50%); N, (3.64%);

Example 9

Synthesis of Compound Tp88

3-(1-Adamantyl)-4-methoxybenzoyl chloride was used as a starting material to synthesize Compound Tp88 according to the method of Example 6. Compound Tp88: light yellow powdery crystals (ethyl acetate); melting point 142° C.; $^1$H-NMR (400 MHz, DMSO-$d_6$, 30° C.) 10.16 (s, 1H), 7.83 (dd, J=8.6, 2.2 Hz, 1H), 7.73 (d, J=2.4 Hz, 1H), 7.72 (d, J=12.2 Hz, 1H), 7.22 (d, J=12.2 Hz, 2H), 7.08 (d, J=8.8 Hz, 1H), 3.88 (s, 3H), 2.07 (s, 6H), 2.05 (s, 3H), 1.74 (s, 6H); Anal. Calcd. for $C_{25}H_{27}N_1O_4.H_2O$ C, (70.90%); H, (6.90%); N, (3.31%); Found C, (71.19%); H, (6.94%); N, (3.31%);

Example 10

Synthesis of Compound Tp90

(E)-(5,6,7,8-Tetrahydro-5,5,8,8-tetramethylnaphthalen-2-yl)acrylic acid chloride was used as the starting material to synthesize Compound Tp90 according to the method of Example 6. Compound Tp90: yellow scaly crystals (ethanol/water); melting point 149° C.; $^1$H-NMR (400 MHz, DMSO-$d_6$, 30° C.) 10.23 (s, 1H), 7.82 (d, J=12.2 Hz, 2H), 7.56 (d, J=15.6 Hz, 1H), 7.56 (s, 1H), 7.34-7.42 (m, 2H), 7.25 (d, J=12.2 Hz, 1H), 6.75 (d, J=15.9 Hz, 1H), 3.65 (s, 4H), 1.27 (s, 6H), 1.25 (s, 6H); Anal. Calcd. for $C_{24}H_{27}N_1O_3.1/4H_2O$ C, (75.46%); H, (7.25%); N, (3.67%); Found C, (75.47%); H, (7.31%); N, (3.59%);

Example 11

Synthesis of Compound Tp93

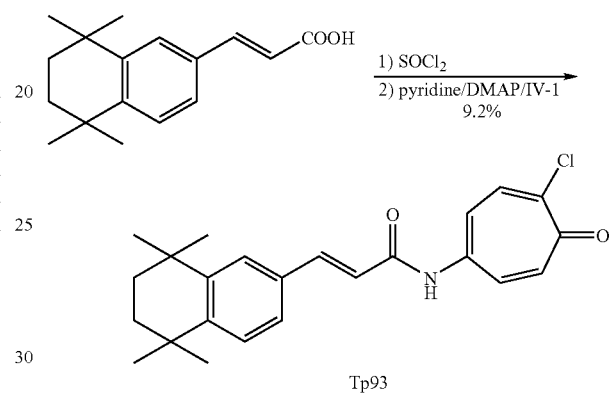

Tp93

(E)-(5,6,7,8-Tetrahydro-5,5,8,8-tetramethylnaphthalen-2-yl)acrylic acid (355 mg, 1.45 mmol) was suspended in thionyl chloride (1.73 g) and anhydrous benzene (5 ml) and refluxed. After 2 hours, the solvent was evaporated, and the residue was added with Compound IV-1 (400 mg, 1.45 mmol), suspended in anhydrous pyridine (5 ml), added with DMAP (53 mg, 0.44 mmol) and stirred at 100° C. After 20 minutes, the reaction solution was added with water and extracted with ethyl acetate, and the organic layer was washed with 2 N hydrochloric acid and saturated brine, dehydrated over $MgSO_4$ and then concentrated. The residue was purified by silica gel column chromatography (ethyl acetate:n-hexane=1:1) to obtain Compound Tp93 (48 mg, 9.2%). Compound Tp93: yellow prisms (ethyl acetate); melting point 241° C.; $^1$H-NMR (400 MHz, DMSO-$d_6$, 30° C.) 10.05 (s, 1H), 7.99 (d, J=11.0 Hz, 1H), 7.91 (dd, J=11.0, 2.2 Hz, 1H), 7.60 (d, J=16.1 Hz, 1H), 7.58 (d, J=2.2 Hz, 1H), 7.55 (dd, J=13.2, 2.2 Hz, 1H), 7.36-7.42 (m, 2H), 7.24 (d, J=13.2 Hz, 1H), 6.78 (d, J=15.7 Hz, 1H), 1.65 (s, 4H), 1.27 (s, 6H), 1.24 (s, 6H)

Example 12

Synthesis of Compound Tp95

(E,E)-5-(5,6,7,8-Tetrahydro-5,5,8,8-tetramethylnaphthalen-2-yl)-2,4-pentadienoic acid chloride was used as the starting material to synthesize Compound Tp95 according to the method of Example 6. Compound Tp95: light yellow prisms (methanol); melting point 216° C.; $^1$H-NMR (400 MHz, $CDCl_3$) 7.71 (d, J=11.9 Hz, 2H), 7.53 (dd, J=10.8 Hz, 14.9 Hz, 1H), 7.29-7.37 (m, 5H), 7.18 (brs, 1H), 6.95 (d, J=15.2 Hz, 1H), 6.85 (dd, J=10.8 Hz, 15.4 Hz, 1H), 6.04 (d, J=14.7 Hz, 1H), 1.70 (s, 4H), 1.31 (s, 6H), 1.29 (s, 6H)

Example 13

Synthesis of Compounds Tp140, Tp141 and Tp145

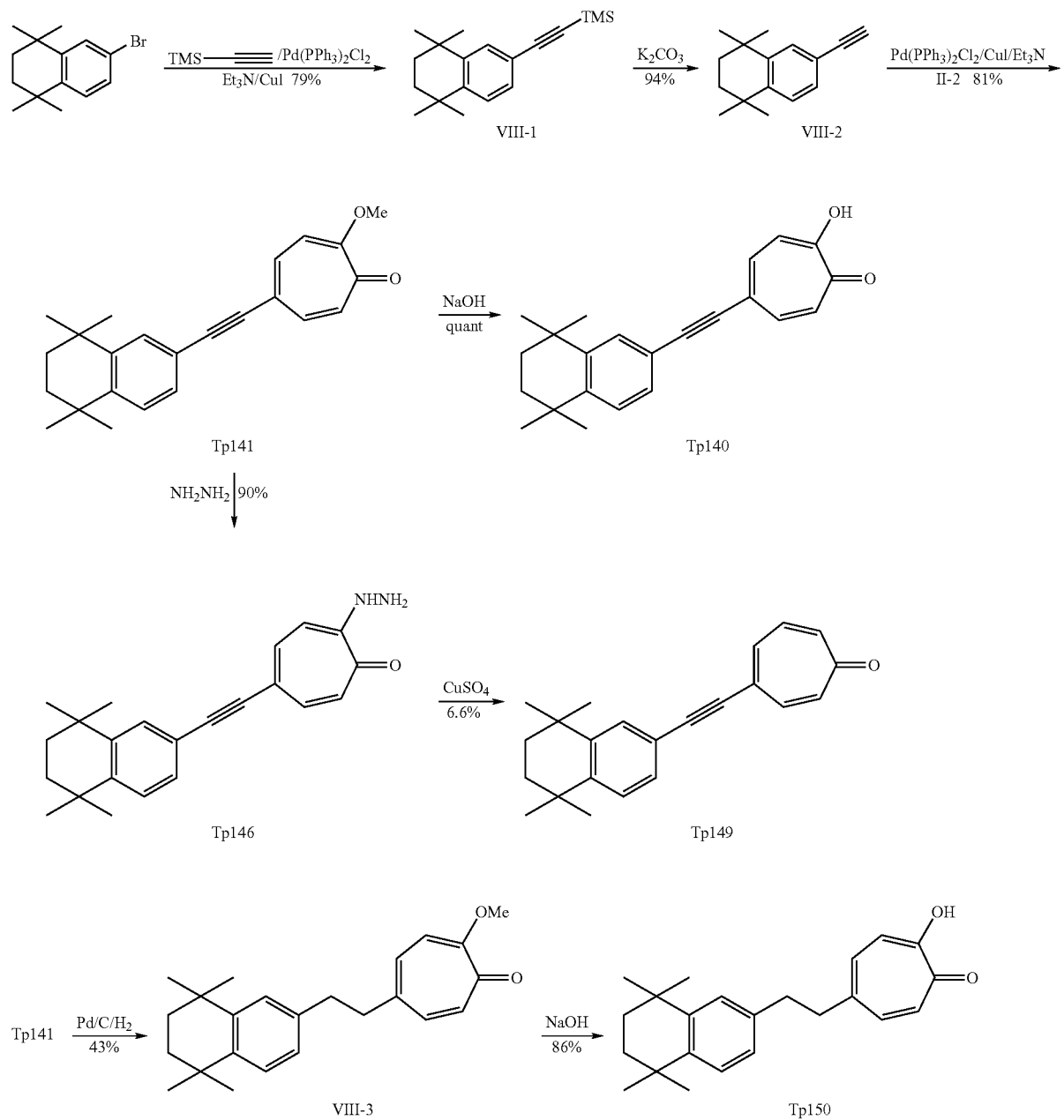

2-Bromo-5,6,7,8-tetrahydro-5,5,8,8-tetramethylnaphthalene (3.00 g, 11.2 mmol) and copper iodide (237 mg, 1.12 mmol) were dissolved in triethylamine (25 ml) under an argon atmosphere. The reaction solution was added with TMS acetylene (3.31 g, 33.7 mmol) and Pd(PPh$_3$)$_2$Cl$_2$ (786 mg, 1.12 mmol) and stirred at 70° C. After 22 hours, the reaction solution was returned to room temperature, extracted with ether and filtered, and the ether layer was washed with water and NH$_4$OH/NH$_4$Cl=9/1 aqueous solution, water, 1 N hydrochloric acid and saturated brine, dehydrated over MgSO$_4$ and then concentrated. The residue was purified by silica gel column chromatography (n-hexane) to obtain Compound VIII-1 (2.51 g, 79%). Compound VIII-1: $^1$H-NMR (400 MHz, CDCL$_3$) 7.40 (s, 1H), 7.21 (s, 2H), 1.66 (s, 4H), 1.26 (s, 6H), 1.25 (s, 6H), 0.24 (s, 9H)

Compound VIII-1 (1.00 g, 3.52 mmol) was dissolved in methanol (15 ml), added with potassium carbonate (97 mg, 0.70 mmol) and stirred at room temperature for 24 hours.

The reaction solution was added with water and extracted with ethyl acetate, and the organic layer was washed with saturated brine, dehydrated over $MgSO_4$ and then concentrated. The residue was purified by silica gel column chromatography (ethyl acetate:n-hexane=1:50) to obtain Compound VIII-2 (700 mg, 94%). Compound VIII-2: 1H-NMR (400 MHz, $CDCL_3$) 7.44 (s, 1H), 7.26 (s, 2H), 3.01 (s, 4H), 1.27 (s, 6H), 1.26 (s, 6H)

Compound VIII-2 (136 mg, 0.64 mmol) and Compound II-2 (160 mg, 0.61 mmol) were suspended in triethylamine (6.0 ml) and bubbled with argon to attain sufficient substitution. This suspension was added with $Pd(PPh_3)_2Cl_2$ (112 mg, 0.16 mmol) and copper iodide (30.5 mg, 0.16 mmol), further bubbled with argon and stirred at room temperature for 24 hours. The reaction solution was filtered through Cerite and extracted with ether, and the organic layer was washed with saturated brine, dehydrated over $MgSO_4$ and then concentrated. The residue was purified by flash silica gel column chromatography (ethyl acetate:n-hexane=2:1) to obtain Compound Tp141 (171 mg, 81%). Compound Tp141: yellow needle crystals (methylene chloride/n-hexane); melting point 139° C.; $^1$H-NMR (400 MHz, DMSO-$d_6$, 30° C.) 7.50 (d, J=1.7 Hz, 1H), 7.41-7.46 (m, 2H), 7.37 (d, J=8.1 Hz, 1H), 7.28 (dd, J=8.1, 2.0 Hz, 1H), 7.02 (d, J=13.0 Hz, 1H), 6.97 (d, J=11.0 Hz, 1H), 3.89 (s, 3H), 1.65 (s, 4H), 1.26 (s, 6H), 1.25 (s, 6H); Anal. Calcd. for $C_{24}H_{26}O_2$ C, (83.20%); H, (7.56%); Found C, (82.93%); H, (7.63%);

Compound Tp141 (125 mg, 0.36 mmol) was dissolved in ethanol (8 ml) and 2 N sodium hydroxide (4 ml) and stirred at room temperature. After 3 hours, the reaction solution was made acidic with 2 N hydrochloric acid and extracted with ethyl acetate, and the organic layer was washed with saturated brine and dehydrated over $MgSO_4$ and then concentrated to obtain a crude product of Compound Tp140 (123 mg, quant). Compound Tp140: yellow needle crystals (ethyl acetate); melting point 182° C.; $^1$H-NMR (400 MHz, DMSO-$d_6$, 30° C.) 7.53 (d, J=11.7 Hz, 2H), 7.48 (d, J=1.7 Hz, 1H), 7.36 (d, J=8.1 Hz, 1H), 7.26 (dd, J=8.1, 1.8 Hz, 1H), 7.09 (d, J=11.7 Hz, 2H), 1.64 (s, 4H), 1,25 (s, 6H), 1.24 (s, 6H); Anal. Calcd. for $C_{23}H_{24}O_2$ C, (83.10%); H, (7.28%); Found C, (82.83%); H, (7.42%);

2-Bromo-5,6,7,8-tetrahydro-3,5,5,8,8-pentamethylnaphthalene was used as a starting material to synthesize Compound Tp145 in the same manner as that used for Compound Tp140. Compound Tp145: yellow prismatic crystals (methylene chloride/n-hexane), melting point 137° C.; $^1$H-NMR (400 M Hz, $CDCl_3$) 7.62 (d, J=12.0 Hz, 2H), 7.42 (s, 1H), 7.30 (d, J=12.0 Hz, 2H), 7.16 (s, 1H), 2.43 (s, 3H), 1.68 (s, 4H), 1.284 (s, 6H), 1.278 (s, 6H); Anal. Calcd. for $C_{24}H_{26}O_2$ C, (83.20%); H, (7.56%); Found C, (82.92%); H, (7.73%);

Example 14

Synthesis of Compounds Tp146 and Tp149

Compound Tp141 (332 mg, 0.96 mmol), methanol (2 ml), water (2 ml) and 80% hydrazine hydrate (2 ml) were heated on a boiling water bath for about 10 minutes. The reaction solution was left stand for cooling to room temperature and then cooled with ice, and the precipitates were collected by filtration, sufficiently washed with water and dried under reduced pressure to obtain a crude product of Compound Tp146 (299 mg, 90%). Compound Tp146: $^1$H-NMR (400 MHz, DMSO-$d_6$, 30° C.) 9.19 (s, 1H), 7.48 (dd, J=11.5, 1.7 Hz, 1H), 7.41 (d, J=1.7 Hz, 1H), 7.36 (dd, J=12.2, 1.7 Hz, 1H), 7.32 (d, J=8.3 Hz, 1H), 7.21 (dd, J=8.0, 1.7 Hz, 1H), 6.99 (d, J=11.2 Hz, 1H), 6.74 (d, J=12.0 Hz, 1H), 5.00 (bs, 2H), 1.64 (s, 4H), 1.25 (s, 6H), 1.23 (s, 6H)

Compound Tp146 (250 mg, 0.72 mmol) was suspended in acetic acid (1 ml) and water (4 ml) and refluxed by heating. The suspension was added with a hot 10% copper sulfate solution (8 ml) and stirred. Thirty minutes after ceasing of the gas generation, the reaction solution was cooled to room temperature and extracted with ethyl acetate, and the organic layer was washed with 2 N hydrochloric acid and saturated brine, dried over $MgSO_4$ and then concentrated. The residue was purified by flash silica gel column chromatography (methylene chloride:ethyl acetate=100:1) to obtain Compound Tp149 (15 mg, 6.6%). Compound Tp149: $^1$H-NMR (400 MHz, $CDCL_3$) 7.45 (d, J=1.7 Hz, 1H), 7.30 (d, J=10.7 Hz, 1H), 7.28 (d, J=10.3 Hz, 1H), 7.22-7.26 (m, 2H), 7.08 (dd, J=12.0, 8.5 Hz, 1H), 6.97-7.003 (m, 2H), 1.57 (s, 4H), 1.30 (s, 6H), 1.28 (s, 6H)

Example 15

Synthesis of Compound Tp150

Compound Tp141 (80 mg, 0.23 mmol) was dissolved in ethanol (5 ml) and added with Pd/C (20 mg) to perform catalytic hydrogen reduction at room temperature. After 2 hours, the reaction solution was filtered to remove the insoluble matter, and the solvent was concentrated. The residue was purified by flash silica gel column chromatography (ethyl acetate:n-hexane=2:1) to obtain Compound VIII-3 (35 mg, 43%). Compound VIII-3: $^1$H-NMR (400 MHz, $CDCL_3$) 7.23 (d, J=8.3 Hz, 1H), 7.22 (d, J=11.0 Hz, 1H), 7.14 (dd, J=12.4, 2.0 Hz, 1H), 7.00 (d, J=2.0 Hz, 1H), 6.94 (dd, J=8.1, 2.0 Hz, 1H), 6.85 (d, J=10.2 Hz, 1H), 6.64 (d, J=10.5 Hz, 1H), 3.92 (s, 3H), 2.83 (s, 4H), 1.66 (s, 4H), 1.27 (s, 6H), 1.22 (s, 6H)

Compound VIII-3 (34 mg, 0.097 mmol) was dissolved in ethanol (2 ml), added with 2 N sodium hydroxide (1 ml) and stirred at room temperature. After 12 hours, the reaction solution was warmed to 70° C. and further stirred for 6 hours. The reaction solution was made acidic with 2 N hydrochloric acid and extracted with ethyl acetate, and the organic layer were washed with saturated brine, dried over $MgSO_4$ and then concentrated to obtain a crude product of Compound Tp150 (28 mg, 86%). Compound Tp150: light yellow scaly crystals (ethanol/water), melting point 138° C.; $^1$H-NMR (400 MHz, DMSO-$d_6$, 30° C.) 7.29 (d, J=11.5 Hz, 2H), 7.19 (d, J=8.3 Hz, 1H), 7.12 (d, J=11.7 Hz, 2H), 7.05 (d, J=2.0 Hz, 1H), 6.96 (dd, J=8.3, 2.0 Hz, 1H), 2.70-2.85 (m, 4H), 1.60 (s, 4H), 1.20 (s, 6H), 1.17 (s, 6H); Anal. Calcd. for $C_{23}H_{28}O_2 \cdot 1/4 H_2O$ C, (81.02%); H, (8.42%); Found C, (80.85%); H, (8.28%);

Example 16

Synthesis of Compound Tp155

1-Bromo-3,5-di-(tert-butyl)benzene was used as a starting material to synthesize Compound Tp155 according to the method of Example 15. Compound Tp155: yellow needle crystals (ethanol); melting point 204° C.; $^1$H-NMR (400 MHz, DMSO-$d_6$, 30° C.) 7.60 (d, J=11.7 Hz, 2H), 7.45 (t, J=1.7 Hz, 1H), 7.36 (d, J=1.7 Hz, 2H), 7.16 (d, J=12.0 Hz, 2H), 1.29 (s, 18H); Anal. Calcd. for $C_{23}H_{26}O_2$ C, (82.60%); H, (7.84%); Found C, (82.46%); H, (7.93%);

Example 17

Synthesis of Compound Tp160

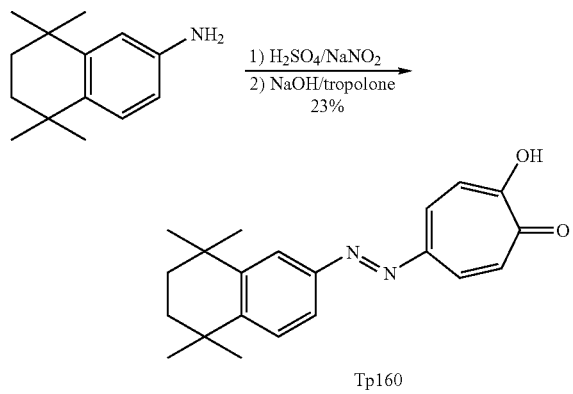

2-Amino-5,6,7,8-tetrahydro-5,5,8,8-tetramethylnaphthalene (102 mg, 0.50 mmol) was added with 30% sulfuric acid (2 ml) and heated with stirring. Soon after the compound was dissolved, the solution was cooled with ice. The reaction solution was added with sodium nitrate (70 mg) and water (2 ml) and stirred. Then, the solution was added with a solution of tropolone (70 mg, 0.57 mmol) dissolved in 10% sodium hydroxide (2 ml) and stirred. After the reaction was completed, the reaction solution was poured into water and extracted with methylene chloride. The organic layer was dried over sodium sulfate, and then the solvent was evaporated. The residue was purified by ODS flash column chromatography (methanol) to obtain Compound Tp160 (38 mg, 23%). Compound Tp160: red needle crystals (methanol/methylene chloride); melting point 185° C.; $^1$H-NMR (400 MHz, CD$_3$OD) 8.21 (dd, J=1.6 Hz, 10.7 Hz, 2H), 7.90 (d, J=2.0 Hz, 1H), 7.65 (dd, J=2.0 Hz, 8.4 Hz, 1H), 7.49 (dd, J=1.3 Hz, 10.5 Hz, 2H), 7.45 (d, J=8.4 Hz, 1H), 1.74 (s, 4H), 1.37 (s, 6H), 1.33 (s, 6H)

Example 18

Synthesis of Compound Tp170

3,5-Di(tert-butyl)aniline was used as a starting material to synthesize Compound Tp170 according to the method of Example 17. Compound Tp170: orange needle crystals (ethanol); melting point 199-201° C.; $^1$H-NMR (400 MHz, DMSO-d$_6$, 30° C.) 8.12 (d, J=12.0 Hz, 2H), 7.71 (d, J=1.7 Hz, 2H), 7.61 (d, J=1.7 Hz, 1H), 7.36 (d, J=11.7 Hz, 2H), 1.35 (s, 18H); Anal. Calcd. for C$_{21}$H$_{26}$N$_2$O$_2$ C, (74.53%); H, (7.74%); N, (8.28%); Found C, (74.38%); H, (7.80%); N, (8.19%);

Example 19

Synthesis of Compound Tp175

3,5-Di(tert-butyl)aniline and 4-isopropyltropolene were used as starting materials to synthesized Compound Tp175 Compounded according to the method of Example 17. Compound Tp175: red needle crystals (ethanol/water); melting point 145° C.; $^1$H-NMR (400 MHz, DMSO-d$_6$, 30° C.) 7.91 (d, J=12.7 Hz, 1H), 7.88 (s, 1H), 7.50-7.55 (m, 2H), 7.35 (s, 1H), 7.19 (d, J=12.7 Hz, 1H), 4.32 (h, J=6.8 Hz, 1H), 1.69 (s, 4H), 1.32 (s, 6H), 1.29 (s, 3H), 1.28 (s, 6H), 1.28 (s, 3H); Anal. Calcd. for C$_{24}$H$_{30}$N$_2$O$_2$ C, (76.16%); H, (7.99%); N, (7.40%); Found C, (75.88%); H, (7.96%); N, (7.44%);

Example 20

Synthesis of Compound Tp180

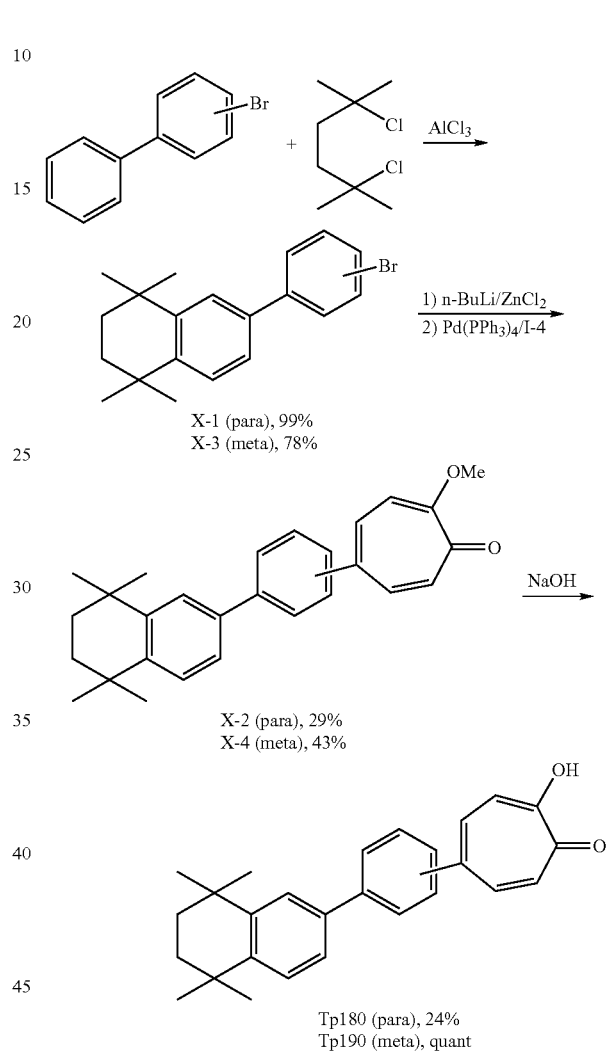

2,5-Dichloro-2,5-dimethylhexane (1.73 g, 9.48 mmol) and 4-bromobiphenyl (2.00 g, 8.58 mmol) were dissolved in methylene chloride (10 ml) and gradually added with aluminum chloride (63 mg) with stirring under ice cooling. After the reaction solution was stirred for 7 hours at room temperature, the mixture was poured into ice water and extracted with methylene chloride, and the organic layer was washed with water, 2 N hydrochloric acid and saturated brine, dehydrated over MgSO$_4$ and then concentrated. A crude product of Compound X-1 was obtained (2.90 g, 99%). Compound X-1: $^1$H-NMR (400 MHz, CDCL$_3$) 7.53 (d, J=8.6 Hz, 2H), 7.47 (d, J=2.0 Hz, 1H), 7.43 (d, J=8.6 Hz, 2H), 7.37 (d, J=8.3 Hz, 1H), 7.31 (dd, J=8.3, 2.2 Hz, 1H), 1.72 (s, 4H), 1.33 (s, 6H), 1.31 (s, 6H); Anal. Calcd. for C$_{21}$H$_{24}$N$_2$O$_2$.1/4H$_2$O C, (73.98%); H, (7.24%); N, (8.22%); Found C, (74.11%); H, (7.27%); N, (8.28%);

Compound X-1 (275 mg, 0.80 mmol) was dissolved in THF (3 ml), added with a 1.6 M solution of n-BuLi (0.96 mmol) in hexane (0.60 ml) at −78° C. and stirred for 30 minutes. This solution was added to a solution of zinc chloride (109 mg, 0.80 mmol) dissolved in THF (2 ml) and stirred at room temperature. After 1 hour, the reaction solution was added to a solution of Compound I-4 (152 mg, 0.54 mmol) and Pd(PPh$_3$)$_4$ (46 mg, 0.040 mmol) dissolved in THF (4 ml) and stirred at room temperature. After 4.5 hours, the reaction solution was added with water and extracted with ethyl acetate, and the organic layer was washed with 2 N hydrochloric acid and saturated brine, dehydrated over MgSO$_4$ and then concentrated. The residue was purified by flash silica gel column chromatography (ethyl acetate:n-hexane=2:1 and methylene chloride:ethyl acetate=3:2) to obtain Compound X-2 (91 mg, 29%). Compound X-2: $^1$H-NMR (400 MHz, CDCl$_3$) 7.66 (d, J=8.3 Hz, 2H), 7.60 (dd, J=12.7, 2.0 Hz, 1H), 7.52-7.56 (m, 3H), 7.33-7.41 (m, 3H), 7.36 (dd, J=12.4, 2.0 Hz, 1H), 6.88 (d, J=10.5 Hz, 1H), 4.01 (s, 3H), 1.74 (s, 4H), 1.36 (s, 6H), 1.33 (s, 6H)

Compound X-2 (85 mg, 0.21 mmol) was dissolved in ethanol (8 ml), added with 2 N sodium hydroxide (3 ml) and stirred at room temperature. After 6 hours, the reaction solution was made acidic with 2 N hydrochloric acid and extracted with ethyl acetate, and the organic layer was washed with saturated brine, dehydrated over MgSO$_4$ and then concentrated. The residue was recrystallized from ethyl acetate/n-hexane to obtain Compound Tp180 (20 mg, 24%). Compound Tp180: yellow green needle crystals (ethyl acetate/n-hexane); melting point 212° C.; $^1$H-NMR (400 MHz, DMSO-d$_6$, 30° C.) 7.73 (d, J=8.3 Hz, 2H), 7.71 (d, J=10.8 Hz, 2H), 7.65 (d, J=8.3 Hz, 2H), 7.59 (d, J=1.6 Hz, 1H), 7.45 (dd, J=8.3, 1.6 Hz, 1H), 7.40 (dd, J=8.0 Hz, 1H), 1.67 (s, 4H), 1.31 (s, 6H), 1.27 (s, 6H)

Example 21

Synthesis of Compound Tp190

3-Bromobiphenyl was used as a starting material to synthesize Compound Tp190 according to the method of Example 20. Compound Tp190: white powder (ethyl acetate/n-hexane), melting point 140° C.; $^1$H-NMR (400 MHz, DMSO-d$_6$, 30° C.) 7.75 (d, J=12.0 Hz, 2H), 7.75 (bs, 1H), 7.63 (dt, J=4.4, 7.3 Hz, ,1H), 7.60 (d, J=2.0 Hz, 1H), 7.53 (d, J=4.9 Hz, 2H), 7.45 (dd, J=8.3, 2.0 Hz, 1H), 7.40 (d, J=8.3 Hz, 1H), 7.30 (d, J=11.8 Hz, 2H), 1.67 (s, 4H), 1.31 (s, 6H), 1.27 (s, 6H)

Example 22

Synthesis of Compound Tp200

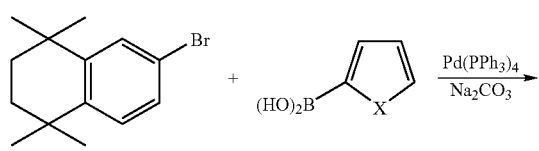

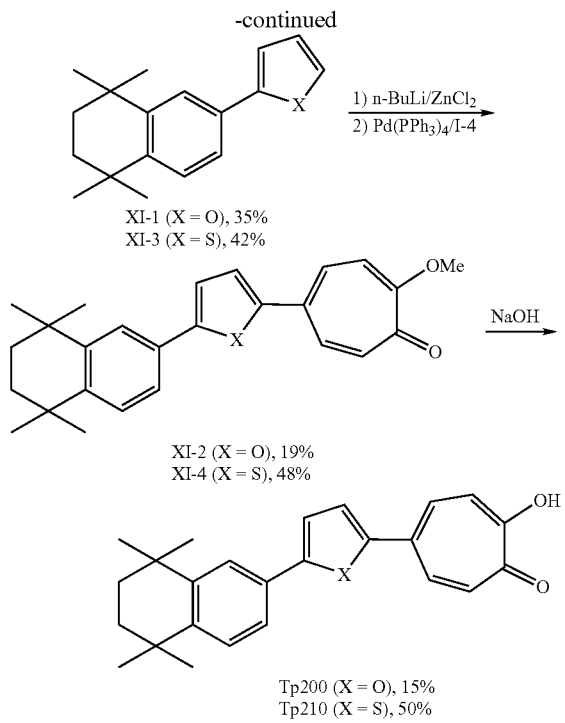

2-Bromo-5,6,7,8-tetrahydro-5,5,8,8-tetramethylnaphthalene (3.00 g, 11.2 mmol) and Pd(PPh$_3$)$_4$ (416 mg, 0.36 mmol) were dissolved in dimethoxyethane (3.6 ml) under an argon atmosphere and stirred for 10 minutes. The reaction solution was added with 2-furanboronic acid (1.45 g, 12.9 mmol), immediately added with 1 M aqueous sodium carbonate (28 ml) and refluxed. After 5.5 hours, the reaction solution was cooled to room temperature. The solvent was evaporated, and the residue was added with water and extracted with ether. The insoluble solids were removed by filtration, and the filtrate was washed with saturated brine, dehydrated over MgSO$_4$ and then concentrated. The residue was purified by silica gel column chromatography (ethyl acetate:n-hexane=1:50) to obtain Compound XI-1 (1.00 g, 35%). Compound XI-1: $^1$H-NMR (400 MHz, CDCL$_3$) 7.61 (d, J=2.0 Hz, 1H), 7.44 (d, J=1.1 Hz, 1H), 7.42 (dd, J=8.1, 2.0 Hz, 1H), 7.31 (d, J=8.3 Hz, 1H), 6.58 (d, J=3.4 Hz, 1H), 6.44 (dd, J=3.1, 1.1 Hz, 1H), 1.70 (s, 4H), 1.33 (s, 6H), 1.29 (s, 6H)

Compound XI-1 (497 mg, 1.96 mmol) was dissolved in THF (4 ml), added with a 1.6 M solution of n-BuLi (2.94 mmol) in hexane (1.84 ml) at −78° C. and stirred for 30 minutes. This solution was added to a solution of zinc chloride (267 mg, 1.96 mmol) dissolved in THF (4 ml) and stirred at room temperature. After 1 hour, the reaction solution was added to a solution of Compound I-4 (370 mg, 1.30 mmol) and Pd(PPh$_3$)$_4$ (75 mg, 0.065 mmol) dissolved in THF (6 ml) and stirred at room temperature. After 1.5 hours, the reaction solution was added with water and extracted with ethyl acetate, and the organic layer was washed with 2 N hydrochloric acid and saturated brine, dehydrated over MgSO$_4$ and then concentrated. The residue was purified by flash silica gel column chromatography (ethyl acetate) to obtain Compound XI-2 (142 mg, 19%). Compound XI-2: $^1$H-NMR (400 MHz, DMSO-d$_6$, 30° C.) 7.81 (dd. J=12.7, 2.0 Hz, 1H), 7.71 (d, J=1.7 Hz, 1H), 7.69

(dd, J=10.3, 1.7 Hz, 1H), 7.54 (dd, J=8.3 1.9 Hz, 1H), 7.39 (d, J=8.3 Hz, 1H), 7.15 (d, J=3.7 Hz, 1H), 7.12 (d, J=10.5 Hz, 1H), 7.09 (d, J=12.9 Hz, 1H), 7.07 (d, J=3.7 Hz, 1H), 3.89 (s, 3H), 1.66 (s, 4H), 1.31 (s, 6H), 1.26 (s, 6H)

Compound XI-2 (135 mg, 0.35 mmol) was dissolved in ethanol (4 ml), added with 2 N sodium hydroxide (1.5 ml) and stirred at room temperature. After 2 hours, ethanol was evaporated, and the residue was added with 2 N sodium hydroxide. The precipitates were collected by filtration and sufficiently washed with ethyl acetate. The crude crystals were suspended in water, and the suspension was made acidic with 2 N hydrochloric acid and extracted with ethyl acetate. The organic layer was washed with saturated brine, dehydrated over $MgSO_4$ and then concentrated. A crude product of Compound Tp200 was obtained (19 mg, 15%). Compound Tp200: orange powder (ethanol/water); melting point 173° C.; $^1$H-NMR (400 MHz, DMSO-$d_6$, 30° C.) 7.91 (d, J=12.0 Hz, 2H), 7.70 (d, J=1.7 Hz, 1H), 7.55 (dd, J=8.0, 2.0 Hz, 1H), 7.38 (d, J=8.3 Hz, 1H), 7.28 (d, J=12.0 Hz, 2H), 7.16 (d, J=3.7 Hz, 1H), 7.08 (d, J=3.7 Hz, 1H), 1.66 (s, 4H), 1.32 (s, 6H), 1.26 (s, 6H); Anal. Calcd. for $C_{25}H_{26}O_3 \cdot 1/4 H_2O$ C, (79.23%); H, (7.05%); Found C, (79.43%); H, (7.12%);

Example 23

Synthesis of Compound Tp210

2-Thiopheneboronic acid was used as a starting material to synthesize Compound Tp210 according to the method of Example 22. Compound Tp210: yellow needle crystals (ethyl acetate/n-hexane); melting point 176° C.; $^1$H-NMR (400 MHz, DMSO-$d_6$, 30° C) 7.80 (d, J=12.2 Hz, 2H), 7.57 (d, J=3.9 Hz, 1H), 7.51 (d, J=3.9 Hz, 1H), 7.42 (dd, J=8.3, 2.2 Hz, 1H), 7.37 (d, J=8.6 Hz, 1H), 7.24 (d, J=12.0 Hz, 1H), 1.66 (s, 4H), 1.29 (s, 6H), 1.25 (s, 6H); Anal. Calcd. for $C_{25}H_{26}O_2S_1$ C, (76.89%); H, (6.71%); Found C, (76.68%); H, (6.84%);

Example 24

Synthesis of Compound Tp250

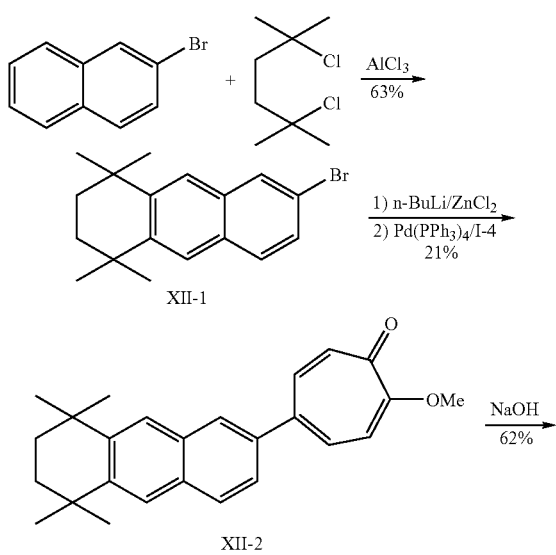

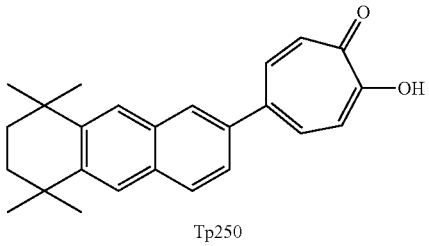

2-Bromonaphthalene (3.00 g, 14.5 mmol) and 2,5-dichloro-2,5-dimethylhexane (2.92 g, 15.9 mmol) were suspended in anhydrous methylene chloride (24 ml) and added with aluminum chloride under ice cooling (300 mg). After the reaction solution was stirred for 6 hours, the mixture was poured into ice water at room temperature and extracted with ethyl acetate, and the organic layer was washed with water, saturated aqueous sodium hydrogencarbonate and saturated brine, dehydrated over $MgSO_4$ and then concentrated. The crude crystals were suspended in ether, and the insoluble solids were removed by filtration. The filtrate was concentrated and purified by silica gel column chromatography (n-hexane) to obtain Compound XII-1 (2.88 g, 63%). Compound XII-1: $^1$H-NMR (400 MHz, $CDCL_3$) 7.90 (d, J=2.0 Hz, 1H), 7.73 (s, 1H), 7.67 (s, 1H), 7.59 (d, J=8.6 Hz, 1H), 7.41 (dd, J=9.4, 2.0 Hz, 1H), 1.76 (s, 4H), 1.38 (s, 6H), 1.38 (s, 6H)

Compound XII-1 (796 mg, 2.51 mmol) was dissolved in THF (5 ml), added with n-butyl lithium (1.6 M solution in hexane) (2.35 ml, 3.77 mmol) at −78° C. and stirred for 30 minutes. This solution was added to a solution of zinc(II) chloride (342 mg, 2.51 mmol) dissolved in THF (4 ml) and stirred at room temperature for 1 hour. Further, this solution was added to a solution of Compound I-4 (415 mg, 1.67 mmol) and Pd(PPh$_3$)$_4$ (96 mg, 0.08 mmol) dissolved in THF (7 ml) and stirred at room temperature. After 2 hours, the reaction solution was added with water and extracted with ethyl acetate, and the organic layer was washed with 2 N hydrochloric acid and saturated brine, dehydrated over $MgSO_4$ and then concentrated. The residue was purified by flash silica gel column chromatography (ethyl acetate) to obtain Compound XII-2 (198 mg, 21%). Compound XII-2: $^1$H-NMR (400 MHz, DMSO-$d_6$, 30° C.) 8.02 (s, 1H), 7.94 (s, 1H), 7.90 (s, 1H), 7.89 (d, J=9.3 Hz, 1H), 7.75 (dd, J=12.9, 2.2 Hz, 1H), 7.49-7.63 (m, 2H), 7.17 (d, J=12.7 Hz, 1H), 7.11 (d, J=10.7 Hz, 1H), 3.90 (s, 3H), 1.74 (s, 4H), 1.37 (s, 12H)

Compound XII-2 (150 mg, 0.40 mmol) was dissolved in ethanol (7 ml), added with 2 N sodium hydroxide (3 ml) and stirred at 70° C. After 30 minutes, ethanol was evaporated, and the residue was added with 2 N sodium hydroxide to sufficiently deposit crystals. The crystals were collected by filtration, and this salt was suspended in water, made acidic with 2 N hydrochloric acid and extracted with ethyl acetate. The organic layer was washed with saturated brine, dehydrated over $MgSO_4$ and then concentrated. A crude product of Compound Tp250 was obtained (89 mg, 62%). Compound Tp250: light yellow scaly crystals (ethyl acetate/n-hexane); melting point 192° C.; $^1$H-NMR (400 MHz, DMSO-$d_6$, 30° C.) 8.03 (s, 1H), 7.95 (s, 1H), 7.90 (s, 1H), 7.89 (d, J=9.5 Hz, 1H), 7.78 (d, J=11.9 Hz, 2H), 7.60 (dd, J=8.3, 1.7 Hz, 1H), 7.33 (d, J=11.7 Hz, 2H), 1.74 (s, 4H), 1.37 (s, 12H); Anal. Calcd. for $C_{25}H_{26}O_2$ C, (83.76%); H, (7.31%); Found C, (83.49%); H, (7.52%);

Example 25

Synthesis of Compound Tp260

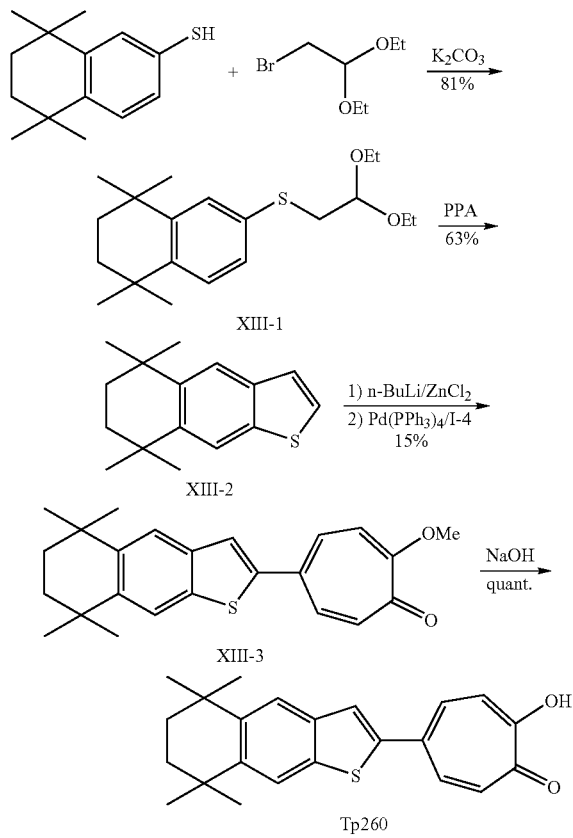

5,6,7,8-Tetrahydro-5,5,8,8-tetramethyl-2-naphthalenethiol (550 mg, 2.50 mmol) was dissolved in DMF (4 ml), added with potassium carbonate (691 mg, 5.00 mmol) and bromoacetaldehyde/diethylacetal (0.45 ml, 591 mmol, 3.00 mmol) at room temperature and stirred at 140° C. After 3 hours, the reaction solution was cooled to room temperature, added with water and extracted with ethyl acetate, and the organic layer was washed with saturated brine, dried over MgSO$_4$ and then concentrated. The residue was purified by flash silica gel column chromatography (ethyl acetate:n-hexane=1:16) to obtain Compound XIII-1 (677 mg, 81%). Compound XIII-1: $^1$H-NMR (400 MHz, CDCL$_3$) 7.32 (d, J=2.0 Hz, 1H), 7.21 (d, J=8.3 Hz, 1H), 7.15 (dd, J=8.3, 2.2 Hz, 1H), 4.64 (t, J=5.6 Hz, 1H), 3.66 (q, J=7.1 Hz, 2H), 3.54 (q, J=7.1 Hz, 2H), 3.10 (d, J=5.6 Hz, 2H), 1.66 (s, 4H), 1.26 (s, 6H), 1.25 (s, 6H), 1.19 (t, J=7.1 Hz, 6H)

Compound XIII-2 (673 mg, 2.00 mmol) was dissolved in toluene (2.5 ml), added to PPA (2.0 g) and stirred at 90° C. After 1 hour, the reaction solution was cooled to room temperature, added with water and extracted with ethyl acetate, and the organic layer was washed with saturated brine, dried over MgSO$_4$ and then concentrated. The residue was purified by flash silica gel column chromatography (methylene chloride:n-hexane=1:10) to obtain Compound XIII-2 (309 mg, 63%). Compound XIII-2: $^1$H-NMR (400 MHz, CDCL$_3$) 7.82 (s, 1H), 7.77 (s, 1H), 7.31 (d, J=5.4 Hz, 1H), 7.22 (d, J=4.9 Hz, 1H), 1.75 (s, 4H), 1.36 (s, 6H), 1.35 (s, 6H)

Compound XIII-2 (192 mg, 0.79 mmol) was dissolved in THF (2 ml), added with a 1.6 M solution of n-BuLi (1.19 mmol) in hexane (0.74 ml) at −78° C. and stirred for 30 minutes. This solution was added to a solution zinc chloride (108 mg, 0.79 mmol) dissolved in THF (2 ml) and stirred at room temperature. After 1 hour, the reaction solution was added to a solution of Compound II-2 (149 mg, 0.52 mmol) and Pd(PPh$_3$)$_4$ (30 mg, 0.026 mmol) dissolved in THF (4 ml) and stirred at room temperature. After 3 hours, the reaction solution was added with water and extracted with ethyl acetate, and the organic layer was washed with 2 N hydrochloric acid and saturated brine, dehydrated over MgSO$_4$ and then concentrated. The residue was purified by flash silica gel column chromatography (methylene chloride:ethyl acetate=2:1 and ethyl acetate:n-hexane=2:1) to obtain Compound XIII-3 (34 mg, 15%). Compound XIII-3: $^1$H-NMR (400 MHz, CDCL$_3$) 7.75 (s, 1H), 7.72 (s, 1H), 7.71 (dd, J=12.7, 2.0 Hz, 1H), 7.43 (s, 1H), 7.43 (dd, J=10.5, 2.0 Hz, 1H), 7.30 (d, J=12.7 Hz, 1H), 6.82 (d, J=10.7 Hz, 1H), 3.99 (s, 3H), 1.75 (s, 4H), 1.36 (s, 12H)

Compound XIII-3 (32 mg, 0.085 mmol) was dissolved in ethanol (2 ml), added with 2 N sodium hydroxide (1 ml) and stirred at room temperature. After 3 hours, the reaction solution was made acidic with 2 N hydrochloric acid and extracted with ethyl acetate, and the organic layer was washed with saturated brine, dried over MgSO$_4$ and then concentrated. A crude product of Compound Tp260 was obtained (32 mg, quant). Compound Tp260: brown prismatic crystals (ethyl acetate/n-hexane), melting point 172° C.; $^1$H-NMR (400 MHz, DMSO-d$_6$, 30° C.) 7.91 (s, 1H), 7.81 (d, J=12.0 Hz, 2H), 7.78 (s, 1H), 7.74 (s, 1H), 7.27 (d, J=12.0 Hz, 2H), 1.69 (s, 4H), 1.32 (s, 12H); Anal. Calcd. for C$_{23}$H$_{24}$O$_2$S$_1$ C, (75.79%); H, (6.64%); Found C, (75.49%); H, (6.69%);

Test Example 1

Test for Induction of Cell Differentiation in HL-60 Cells

For each of the compounds of the examples, action for inducing cell differentiation was examined for each alone and in combination with $1\times10^{-7}$ M of HX630. According to the methods described in Japanese Patent Unexamined Publication (KOKAI) No. (Sho)61-76440/1986, differentiation of the cells of promyelocyte leukemia cell strain HL-60 into granulocytic series cells was determined based on morphological change and measurement of ability to reduce nitro blue tetrazolium (NBT). The ratios (%) of differentiated cells shown in the following table are those calculated from NBT reduction ability. HX630 is a retinoid synergist that enhances actions of retinoids, and the concentrations of −8, −7 and −6 mean that each compound was added at concentrations of $1\times10^{-8}$ M, $1\times10^{-7}$ M and $1\times10^{-6}$ M, respectively.

TABLE 2

| | Ratio of cells for which differentiation was induced by each compound alone (%) Concentration | | | Ratio of cells for which differentiation was induced by each compound in combination with $1 \times 10^{-7}$ M of HX630 (%) Concentration | | |
|---|---|---|---|---|---|---|
| Compound | −8 | −7 | −6 | −8 | −7 | −6 |
| Tp05 | 0.6 | 0.5 | 13 | 1.2 | 1.2 | 35 |
| Tp10 | 6.8 | 2.9 | 3.3 | 3 | 2.9 | 5.6 |

TABLE 2-continued

| Compound | Ratio of cells for which differentiation was induced by each compound alone (%) Concentration | | | Ratio of cells for which differentiation was induced by each compound in combination with $1 \times 10^{-7}$ M of HX630 (%) Concentration | | |
|---|---|---|---|---|---|---|
| | -8 | -7 | -6 | -8 | -7 | -6 |
| Tp20 | 2.1 | 1.8 | 2.7 | 4.6 | 3.7 | 2.4 |
| Tp22 | 2.8 | 2.4 | 18 | 2.1 | 3.3 | 78 |
| Tp30 | 1.3 | 1.5 | 1.2 | 2.5 | 2.3 | 20 |
| Tp40 | 1.3 | 0.9 | 2.3 | 1.8 | 2.5 | 2 |
| Tp50 | 1.6 | 2.8 | 5.1 | | | |
| Tp60 | 0.8 | 1.3 | 2.1 | 2.2 | 21.2 | 37.8 |
| Tp80 | 7 | 26 | 21 | 82 | 85 | 79 |
| Tp82 | 0.5 | 1.2 | 1.4 | 1.9 | 7 | 42 |
| Tp84 | 0.7 | 5 | 26 | 15 | 89 | 90 |
| Tp88 | 0.9 | 1.2 | 46 | 2.6 | 14 | 62 |
| Tp90 | 0.7 | 0.9 | 67 | 1.5 | 2.1 | 43 |
| Tp93 | 0.6 | 0.8 | 9 | 3.6 | 0.8 | 40 |
| Tp95 | 0.5 | 0.5 | 0.3 | 0.8 | 0.5 | 1.7 |
| Tp140 | 65 | 73 | 14 | 89 | 93 | 66 |
| Tp141 | 2.2 | 3.3 | 6.4 | 4.1 | 7 | 84 |
| Tp145 | 73 | 76 | 70 | 82 | 75 | 77 |
| Tp146 | 3.6 | 2.2 | 69 | 66 | 91 | 83 |
| Tp149 | 1.4 | 4 | 40 | 3.5 | 85 | 40 |
| Tp150 | 1.5 | 5.4 | 60 | 9 | 80 | 50 |
| Tp155 | 2.7 | 24 | 62.5 | 68 | 89 | 78 |
| Tp160 | 18.5 | 34.4 | 32 | 81 | 84 | 90 |
| Tp170 | 1.1 | 0.8 | 2.3 | 0.5 | 2.3 | 10 |
| Tp175 | 1.9 | 1.2 | 25 | 3 | 2 | 33 |
| Tp180 | 0.9 | 0.5 | 0 | 2.7 | 2.6 | 33 |
| Tp190 | 1.6 | 32 | 0 | 77 | 90 | 50 |
| Tp200 | 2 | 14 | 36 | 77 | 95 | 50 |
| Tp210 | 0.8 | 6 | 11 | 64 | 91 | 91 |
| Tp250 | 63 | 66 | 56 | 91 | 84 | 79 |
| Tp260 | 10 | 20 | 55 | 91 | 83 | 67 |

INDUSTRIAL APPLICABILITY

The compounds of the present invention have retinoid actions and are useful as active ingredients of medicaments for preventive or therapeutic treatments of vitamin A deficiency disease and agents for suppressing action of a physiologically active substance which binds to an intranuclear receptor belonging to the intranuclear receptor super family to exhibit the physiological action.

What is claimed is:

1. A compound represented by the following general formula (I) or a salt thereof:

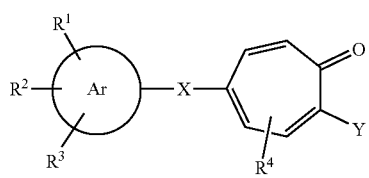

wherein $R^1$, $R^2$, $R^3$ and $R^4$ independently represent hydrogen atom, a $C_{1-10}$ alkyl group, said alkyl group may be substituted, or a $C_{1-6}$ alkoxyl group, and when $R^2$ and $R^3$ are adjacent to each other, they may combine together with carbon atoms of the phenyl group to which $R^2$ and $R^3$ bind to form a 5- or 6-membered ring, said ring may have one or more $C_{1-4}$ alkyl groups or one condensed benzene ring which may have one or more substituents on the ring; the ring represented by Ar represents an aryl ring; X represents a single bond, —N=N—, —CON($R^5$)—, wherein $R^5$ represents hydrogen atom or a $C_{1-6}$ alkyl group, —(C=C)$_n$CON($R^6$)—, wherein n represents an integer of 1 to 3, and $R^6$ represents hydrogen atom or a $C_{1-6}$ alkyl group, —N($R^7$)CON($R^8$)—, $R^7$ and $R^8$ represent hydrogen atom or a $C_{1-6}$ alkyl group, —SO$_2$N($R^9$)—, $R^9$ represents hydrogen atom or a $C_{1-6}$ alkyl group, —N($R^{10}$)—, $R^{10}$ represents hydrogen atom, a $C_{1-6}$ alkyl group, or a $C_{1-6}$ acyl group, a $C_{1-6}$ alkylene group, said alkylene group may contain one or more unsaturated bonds or a cyclic structure, or an aryldiyl group; Y represents hydrogen atom, —OR$^{11}$, $R^{11}$ represents hydrogen atom, a $C_{1-6}$ alkyl group, or a $C_{1-6}$ acyl group, —NHR$^{12}$, $R^{12}$ represents hydrogen atom, a $C_{1-6}$ alkyl group, a $C_{1-6}$ acyl group, or amino group, or a halogen atom.

2. The compound or salt thereof according to claim 1, wherein $R^4$ is hydrogen atom or a $C_{1-6}$ alkyl group, Y is hydrogen atom, hydroxyl group, a $C_{1-6}$ alkoxyl group, hydrazino group, or a halogen atom.

3. A pharmaceutical composition comprising the compound or a physiologically acceptable salt thereof according to claim 1.

4. A method for treating leukemia, comprising administering a pharmaceutical composition according to claim 3 in a therapeutically effective amount.

5. A pharmaceutical composition comprising the compound or a physiologically acceptable salt thereof according to claim 2.

6. A method for treating leukemia, comprising administering a pharmaceutical composition according to claim 5 in a therapeutically effective amount.

7. The compound or salt thereof according to claim 1, is a compound or salt thereof of the following formula:

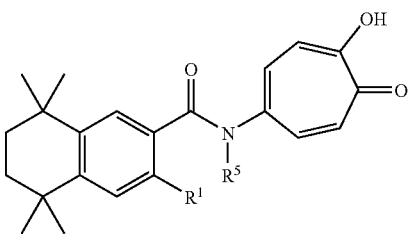

wherein $R^1$ and $R^5$ are hydrogen.

8. A pharmaceutical composition comprising the compound or a physiologically acceptable salt thereof according to claim 7.

9. A method for treating leukemia, comprising administering a pharmaceutical composition according to claim 7 in a therapeutically effective amount.

* * * * *